United States Patent [19]

Cobbs et al.

[11] Patent Number: 5,108,916

[45] Date of Patent: Apr. 28, 1992

[54] **PROCESS FOR STEREOSELECTIVELY HYDROLYZING, TRANSESTERIFYING OR ESTERIFYING WITH IMMOBILIZED ISOZYME OF LIPASE FROM *CANDIDA RUGOSA***

[75] Inventors: Carrington S. Cobbs, Ellicott City; Michael J. Barton, Rockville; Lin Peng, Baltimore; Animesh Goswami, Columbia; Adrien P. Malick, Woodstock; John P. Hamman, Baltimore; Gary J. Calton, Elkridge, all of Md.

[73] Assignee: Rhone-Poulenc Rorer, S.A., Antony, France

[21] Appl. No.: 361,049

[22] Filed: Jun. 5, 1989

[51] Int. Cl.$^5$ .......................... C12P 7/62; C12P 7/42; C12N 11/00; C12N 9/20
[52] U.S. Cl. .................................. 435/135; 435/134; 435/141; 435/146; 435/147; 435/174; 435/177; 435/180; 435/198; 435/280
[58] Field of Search ............... 435/134, 135, 174, 175, 435/177, 180, 188, 198, 280, 814, 815, 94.1, 146, 147

[56] References Cited

U.S. PATENT DOCUMENTS

| | | |
|---|---|---|
| 3,189,529 | 6/1965 | Yamada et al. ...................... 195/62 |
| 4,472,503 | 9/1984 | Matsuo et al. .................. 435/198 X |
| 4,601,987 | 7/1986 | Klibanov et al. ..................... 435/280 |
| 4,650,755 | 3/1987 | Wood et al. .................... 435/180 X |
| 4,818,695 | 4/1989 | Eigtved ............................... 435/134 |
| 4,873,194 | 10/1989 | Sawamura et al. ................ 435/198 |
| 4,897,357 | 1/1990 | Smith et al. ......................... 435/280 |
| 4,923,810 | 5/1990 | Walts et al. .................... 435/280 X |

FOREIGN PATENT DOCUMENTS 1-60392  3/1989  Japan ................................. 435/134

OTHER PUBLICATIONS

Abramowicz et al, *Biotechnology and Bioengineering*, 33:149-156 (Jan., 1989).

Veeraragavan et al, *Biotechnology Letters*, 11(5):345-348 (May, 1989).

Benzonana et al, "On the Positional and Chain Specificities of Candida Cylindracea Lipase", Biochim. Biophys. Acta, 231 (1971) pp. 15-22.

Schifreen et al., "An Investigation of the Kinetic Characteristics of the Lipase From Candida Cylindracea for its Potential in Triglyceride Analysis", Analytical Letters, 12(B1) (1979), pp. 47-69.

Dahod et al., "Carbon Tetrachloride-Promoted Stereo selective Hydrolysis of Methyl-2-Chloropropionate by Lipase", Biotechnology and Bioengineering, vol. 30 (1987), pp. 995-999.

Caldwell et al., "The Metabolic Chiral Inversion and Dispositional Enantioselectivity of the 2-Arylpropionic Acids and Their Biological Consequences", Biochemical Pharmacology, vol. 37, No. 1 (1988), pp. 105-114.

Stokes et al., "Enzyme Reactions in Apolar Solvents: The Resolution of (+)-Sulcatol With Porcine Pancreatic Lipase", Tetrahedron Letters, vol. 28, No. 19 (1987), pp. 2091-2094.

Kodera et al., "Ester Synthesis From α-Substituted Carboxylic Acid Catalyzed by Polyethylene Glycol-Modified Lipase from Candida Cylindracea in Benzene", Biotechnology Letters, vol. 8, No. 12 (1986) pp. 881-884.

(List continued on next page.)

*Primary Examiner*—David M. Naff
*Attorney, Agent, or Firm*—Cushman, Darby & Cushman

[57] ABSTRACT

An immobilized isozyme of Lipase MY or AY from *Candida rugosa* is used for stereoselectively hydrolyzing racemic mixtures of esters of 2-substituted acids, other than 2-halo propionic acids, transesterifying esters or acids or esterify acids or alcohols, at high enantiomeric excess, in an organic solvent. Immobilization of the isozyme may be carried out in the presence of an organic acid such as stearic acid. The immobilized isozyme may be used with a fatty acid or fatty acid ester that increases stereoselectivity or rate of hydrolysis of a mixture of racemic esters.

23 Claims, 9 Drawing Sheets

OTHER PUBLICATIONS

Cambou et al., "Preparative Production of Optically Active Esters and Alcohols Using Esterase-Catalyzed Stereo-specific Transesterification in Organic Media", J. Am. Chem. Soc., 106 (1984), pp. 2687–2692.

Gu et al., "A Facile Enzymatic Resolution Process for the Preparation of (+)-S-(6-Methoxy-2-Naphthyl)-Propionic Acid (Naproxen)", Tetrahedron Letters, vol. 27, No. 16 (1986), 1763–1766.

Nissan Chemical Industries, JP 255917–1986 (Abstract) equivalent to JP 86 202283/31.

Guanti et al., "Enzymes in Asymmetric Synthesis: Effect of Reaction Media on the PLE Catalyzed Hydrolysis of Diesters", Tetrahedron Letters, vol. 27, No. 38 (1986), 4639–4642.

Schreier, Peter (ed.), "Screening of Lipases for Enantiomer Resolution of Secondary Alcohols by Esterification in Organic Medium", *Bioflavour* '87, Proceedings of the International Conference, Wurzburg, Fed. Rep. of Germany, Sep. 29–30, 1987, Berlin (1988), pp. 543–544.

Walts et al., "(R)—Glycidyl Butyrate: Evolution Of A Laboratory Procedure To An Industrial Process", *Biotech U.S.A.* 1987, Proceeding of the Conference held in Santa Clara, Calif., Nov. 1987, Lodon, pp. 91–98.

Calton, Gary J., "Use of Microorganisms and Enzymes in the Synthesis and Production of Optically Active Agricultural Chemicals", *Biotechnology in Agricultural Chemistry*, LeBaron et al. (eds.), ACS Symposium Series 334, Washington, D.C.: American Chemical Society, pp. 181–188.

Sih et al., "The Use of Microbial Enzymes for the Synthesis of Optically Active Pharmaceuticals", *Developments in Industrial Microbiology*, (Journal of Industrial Microbiology, Suppl. No. 3), vol. 29, Ed. G. Pierce, Publ. Elsevier Science Publishers (1988), pp. 221–229.

Cambou et al., "Lipase-Catalyzed Production of Optically Active Acids via Asymmetric Hydrolysis of Esters", *Short Communication* (Applied Biochemistry and Biotechnology), vol. 9 (1984), pp. 255–260.

Akiyama et al., "Enzymes in Organic Synthesis", Chemech (Oct. 1988), pp. 627–634.

Farb et al., "Dependence of pH of the Activity of Pig Liver Esterase", Archives of Biochemistry and Biophysics, vol. 203, No. 1 (Aug. 1980) pp. 227–235.

Elshourbagy, Nabil A. (Ph.D), "DNA-Dependent RNA Polymerases in the Southern Armyworm (Spodoptera Eridania) and Their Role in Microsomal Enzyme Induction" (Order NO. 7809477), Chemistry, Biological, pp. 5900B–5901B.

Technical Service Bulletin, Lipase-My: The Microbial Lipase of *Candida cylindracea* nov. sp. (Meito Sanygo Co., Ltd.).

Technical Bulletin, "Lipase AY Amano 30 derived from *Candida cylindracea*", Lipase PR-7 (Amano International Enzyme Co., Inc., Troy, Va., U.S.A.).

SDS-PAGE of lipase MY, lipase AY and Biocatalyst lipase
SDS-PAGE 10-15% Gel

IEF gel, pI 3-9 of commercial C, rugosa lipases.

*Fig. 3.* SP-TRIS ACRYL M CHROMATOGRAPHY OF LIPASE MY
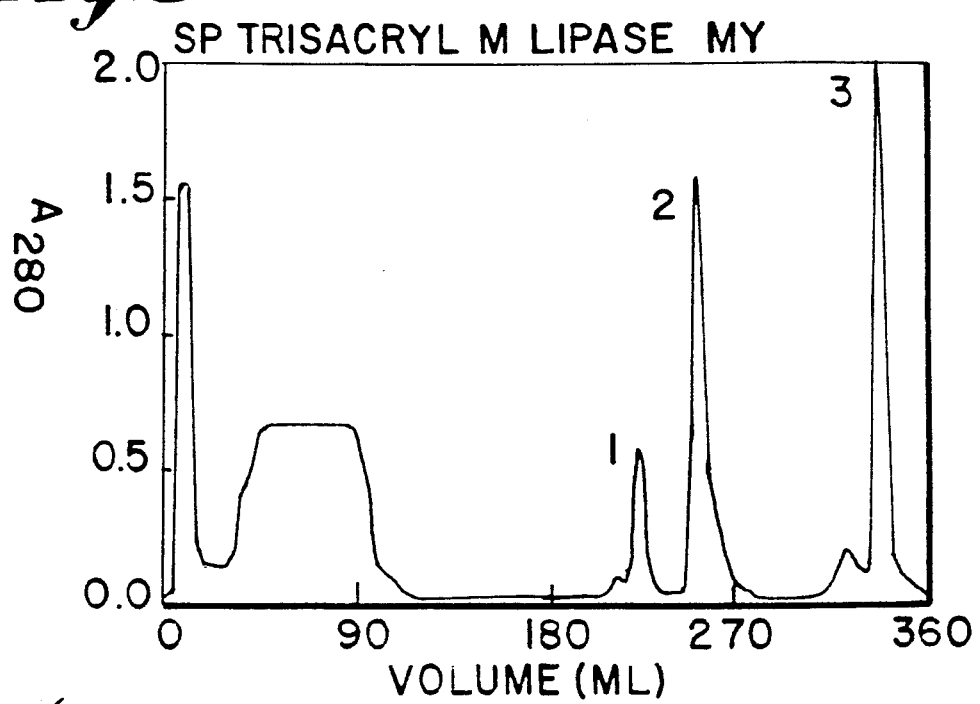
*Fig. 4.*
IEF gel, pi 3-9 of SP-TrisAcryl M lipase MY column fractions
1 2 3 4 5 6 7

Fig. 5. SP-SEPHADEX CHROMATOGRAPHY OF LIPASE MY
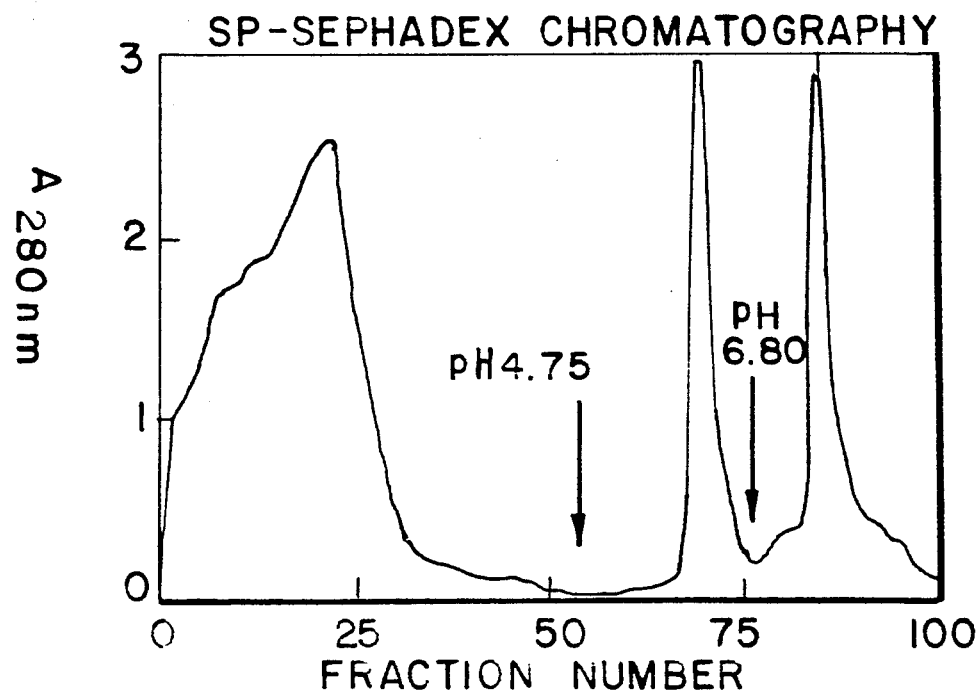
Fig. 6.
IEF Gel, pI 3-9 of SP-TrisAcryILS lipase MY column fractions
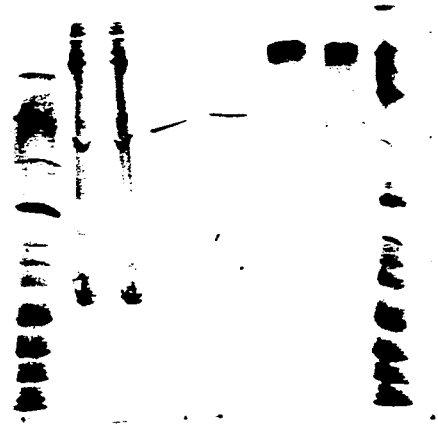
1 2 3 4 5 6 7 8

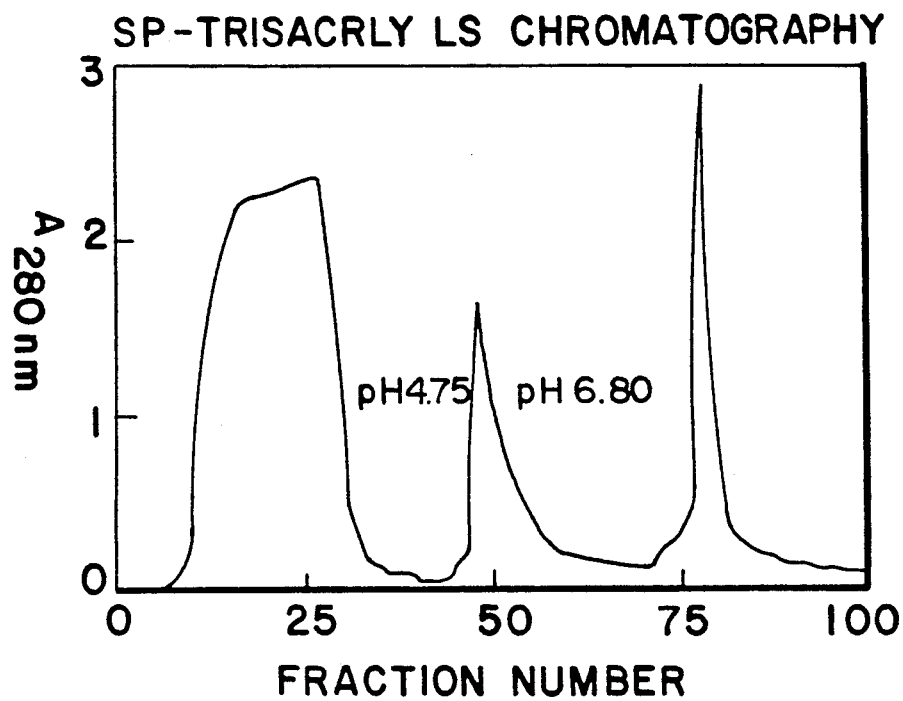
Fig. 7. SP-TRIS ACRYL LS CHROMATOGRAPHY OF LIPASE MY
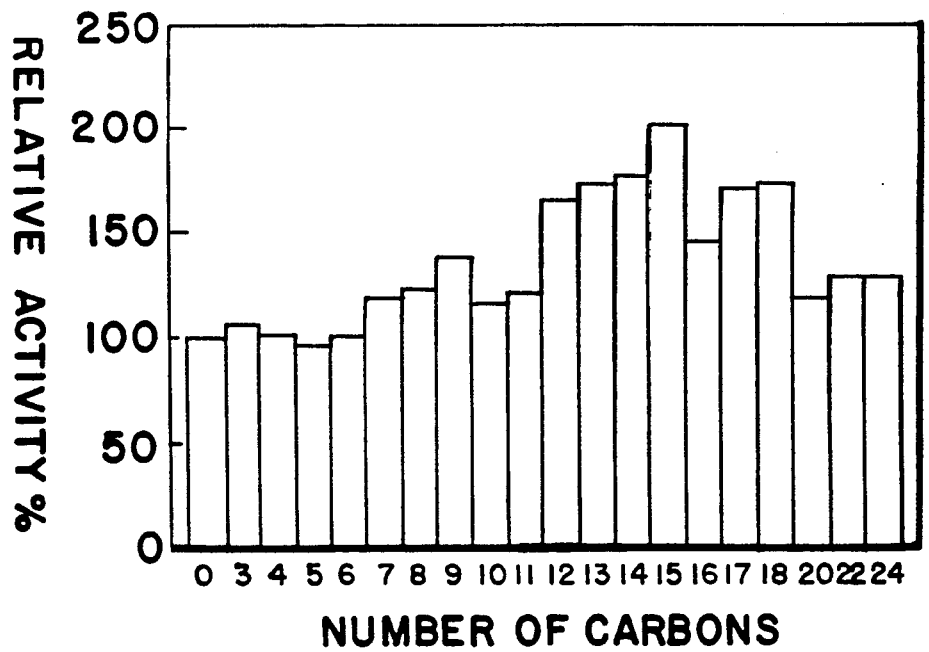
Fig. 8. EFFECT OF ORGANIC ACIDS ON THE IMMOBILIZATION OF LIPASE MY.

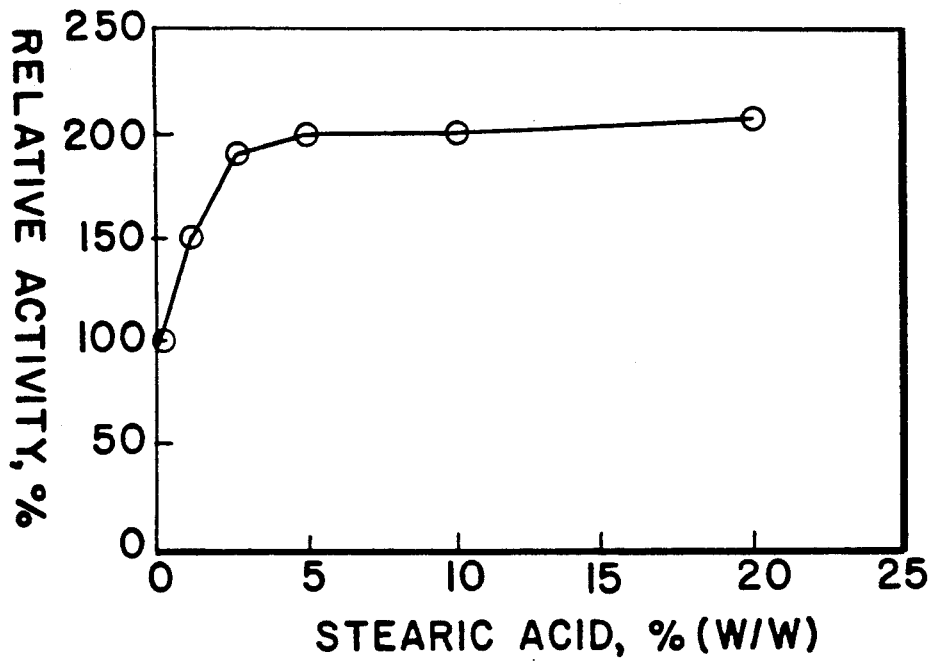
Fig. 9. EFFECT OF STEARIC ACID (0-20%) ON LIPASE MY IMMOBILIZATION.
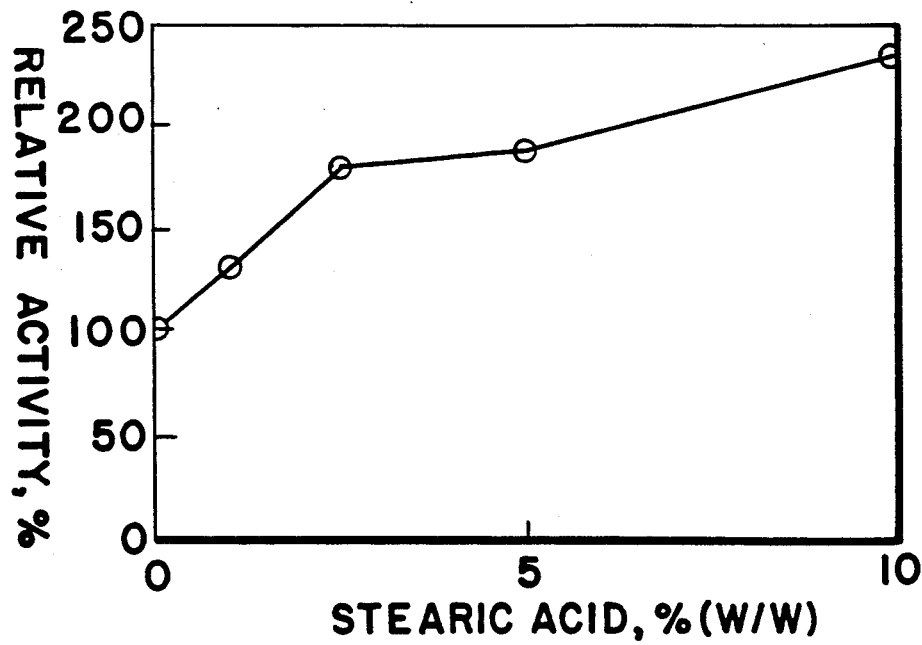
Fig. 10. EFFECT OF STEARIC ACID (0-10%) ON LIPASE MY IMMOBILIZATION.

Fig. 11. STABILITY OF IMMOBILIZED LIPASE CSC-1.
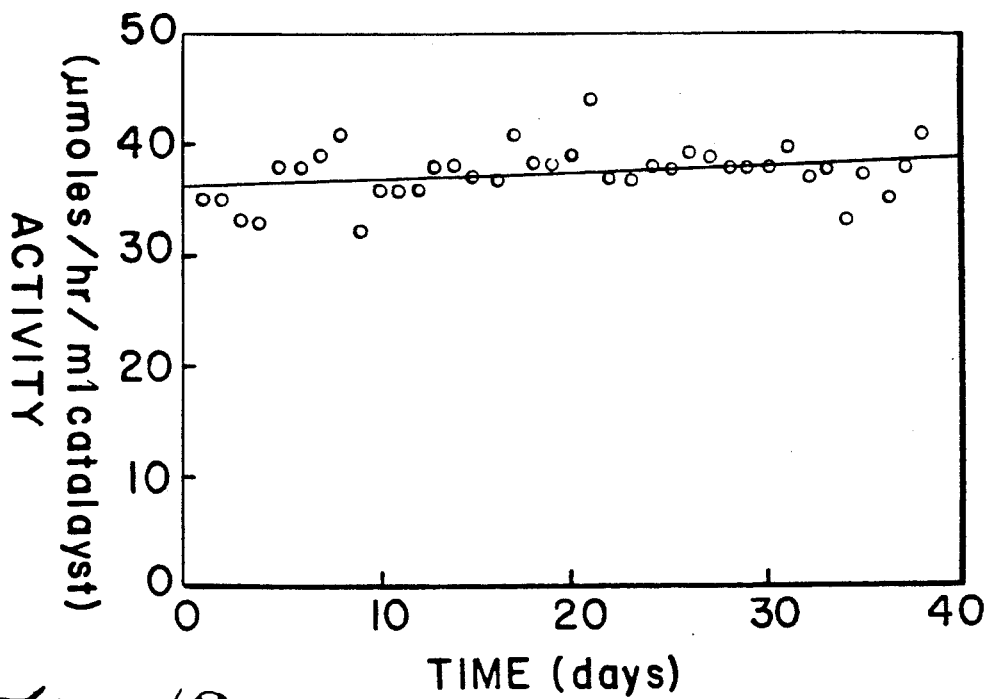
Fig. 12.
SDS-PAGE OF C. rugosa lipases, CSC- and ENZECO Rxx
SDS-PAGE 8-15% Gel
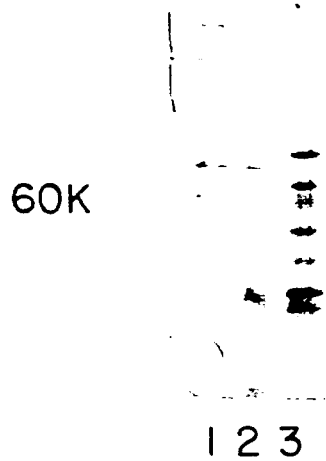

PROCESS FOR STEREOSELECTIVELY HYDROLYZING, TRANSESTERIFYING OR ESTERIFYING WITH IMMOBILIZED ISOZYME OF LIPASE FROM *CANDIDA RUGOSA*

The present invention is concerned with the isolation, immobilization and use of enzymes and isozymes from preparations of lipase from *Candida rugosa*.

BACKGROUND OF THE INVENTION

The use of lipases or esterases to stereoselectively hydrolyze esters has received considerable attention over the past several years. See Cambou B. and A. M. Klibanov, Lipase-Catalyzed Production of Optically Active Acids via Asymmetric Hydrolysis of Esters/Effect of the Alcohol Moiety, Appl Biochem & Biotech 9, 225-260 (1984); Dahod, S. K. and P. Siuta-Mangano, Resolution of Racemic Mixture of Aliphatic Acid Esters, Stauffer Chemical Company, European Patent Application 86104201.8 (03-26-1986) (hereinafter Dahod EPA); Dahod, S. K. and P. Siuta-Mangano, Carbon Tetrachloride-Promoted Stereo Selective Hydrolysis of Methyl-2-Chloropropionate by Lipase, Biotech. & Bioeng. 30, 995-999 (1987) (hereinafter Dahod Biotech); and Walts, A. E., Fox, E. M., and C. B. Jackson, R-Glycidyl Butyrate: Evolution of A Laboratory Procedure to an Industrial Process, Biotech USA 1987, Online International, London. This is due to a desire to produce agricultural or pharmaceutical intermediates with a particular stereo-chemistry where the undesired enantiomer possesses little or none of the activity, but may be responsible for unwanted toxicity. See Calton, G. J., Use of Microorganisms and Enzymes in the Synthesis and Production of Optically Active Agricultural Chemicals, ACS Symposium Series 334 Biotechnology in Agricultural Chemistry, Amer. Chem. Soc., Washington D.C., 1987. A number of propionic acid derivatives which are used in the agricultural and pharmaceutical fields fall into this category. See Dahod EPA; Dahod Biotech; and Calton, and Caldwell, J., Hutt, A. J., and Fournel-Gigleux, S., Metabolic Chiral Inversion and Dispositional Enantioselectivity of the 2-Arylpropionic Acids and Their Biological Consequences, Biochemical Pharmacology 37, 105-114 (1988).

Although a large number of lipases have been evaluated for the resolution of racemic alcohols and/or carboxylic acids, they have not generally met with great success due to enantiospecificities below 95%. It is generally accepted that enantioselectivities above 95% are required for an industrially significant process. See Akiyama, A., Bednarski, M., Kim, M.-J., Simon, E. S., Waldmann, H. and Whitesides, G. M., Enzymes in Organic Synthesis, Chemtech 1988, 627-634 (hereinafter Whitesides). Only a few of the lipases reported in the literature exhibit a high degree of stereospecificity. See Dahod EPA; Dahod Biotech; Walts, Nissan Chem Ind Japanese Pat Appl 8 6-20283/31; Stokes, T. M. and A. C. Oehlschlager, Enzyme Reactions in Apolar Solvents: The Resolution of ($\pm$)-Sulcatol With Porcine Pancreatic Lipase, Tetra. Lett. 28, #19, 2091-2094 (1987); Kodera, Y., Takahashi, K., Nishimura, H., Matsushima, A., Saito, Y., and Y. Inada, Ester Synthesis from -substituted Carboxylic Acid Catalyzed by Polyethylene Glycol-Modified Lipase From *Candida rugosa* in Benzene, Biotech. Lett. 8, 881-884 (1986); and Klibanov, A. M. and Kirchner, G. Enzymatic Production of Optical Isomers of 2-Halopropionic Acids, U.S. Pat. No. 4,601,987, Jul. 22, 1986. Lipases have also been extensively examined for the production of optically active esters from mixtures of acids and/or alcohols and have exhibited good enantioselectivity for esterification with, long chain alcohols. See Klibanov, A. M. and Kirchner, G., Enzymatic Production of Optical Isomers of 2-Halopropionic Acids, U.S. Pat. No. 4,601,987, Jul. 22, 1986; and Cambou B. and Klibanov, A. M., Preparative Production of Optically Active Esters and Alcohols Using Esterase-Catalyzed Stereospecific Transesterification in Organic Media, J. Am. Chem. Soc. 106, 2687-2692 (1984).

The lipase from *Candida rugosa* (formerly known as *Candida cylindracea*) has been used extensively and has been shown to exhibit limited stereospecificity in the hydrolysis of some esters. This enzyme is available commercially from a large number of sources, including Sigma, Meito Sangyo, Biocatalysts, Enzyme Development Corp and Amano. Its production is based on extraction from fermentation broths and cells of *C. rugosa* ATCC #14830. Prior work has shown that the lipase from *Candida rugosa* (Sigma) did not give stereospecific hydrolysis of methyl esters of 2-chloropropionic acid but did give a high enantiomeric excess in the hydrolysis of the octyl ester of 2-chloropropionic acid. See Klibanov, A. M. and Kirchner, G., Enzymatic Production of Optical Isomers of 2-Halopropionic Acids, U.S. Pat. No. 4,601,987, Jul. 22, 1986. Additionally, it has been shown that the synthesis of the octyl ester was absolutely stereospecific. See Cambou B. and Klibanov: A. M., Preparative Production of Optically Active Esters and Alcohols Using Esterase-Catalyzed Stereospecific Transesterification in Organic Media, J. Am. Chem. Soc. 106, 2687-2692 (1984).

It has also been found that in a two phase aqueous/organic mixture at low temperatures (4° C.), one can obtain high optical purity (90% ee) after 30% hydrolysis. Interestingly, heavily chlorinated solvents were superior for this hydrolysis and $CCl_4$ activated the enzyme in the presence of substrate, whereas in the absence of substrate, $CCl_4$ rapidly deactivated the enzyme. See Dahod and SiutaMangano. It has also been shown that the optical purity obtained in the reaction was a function of the extent of hydrolysis, in accordance with earlier predictions and that optical purity decreased rapidly as the reaction neared complete hydrolysis of one of the enantiomers.

Sih and co-workers, (Sih, C. J., Gu, Q-M, Fulling, G., Wu, S.-H and Reddy, D. R. J. Indus. Micro Suppl 3, Develop Ind Micro., 1988, 29, 221-229; Gu, Q.-M., Chen, C.-S. and Sih, C. J. Tet Lett 1986, 27, 1763-1766) have found excellent resolution of the (S) enantiomer of 2-arylpropionic acids, depending on the nature of the aryl substituent. For 2-(6-methoxy-2-naphthyl)propionic acid (naproxen) and p-isobutylhydratropic acid (ibuprofen), the enantiospecificity of *Candida rugosa* lipase was over 98% ee. However, for 2-(3-benzoylphenyl)propionic acid (ketoprofen), the ee was only 51%.

Workers at Nissan Chemical Industries (Nissan Chem Ind Japanese Patent JP-255917 1986) attempted to take advantage of the stereoselective hydrolysis by a preparation of *Candida rugosa* lipase for the production of an aryloxypropionic acid, (R)-(+)-2-(4-hydroxyphenoxy)-propionic acid (R-HPPA); however, they only obtained an 87% ee at 21% hydrolysis in aqueous solution.

The lipase of *Candida rugosa* has been referred to as if it were a single enzyme regardless of its source although recently a separation of the crude enzyme has been published. See Abramowicz, D. A. and Keese, C. R., Enzymatic Transesterifications of Carbonate in Water-Restricted Environments, Biotech. Bioeng. 33, 149-156 (1989). However, it is well known in the literature that many enzymes contain a number of different isozymes with different specifications. Isozymes from pig liver esterase have been isolated. See Farb, D. H., Multiple Forms of Microsomal Porcine Liver Esterase: I. Isolation and Properties, Estimation of Secondary Structure. II. pH Dependence of Rate Contacting Groups, Diss Ab. Int B 38, 5900-5901 (1978); Farb, D. and Jencks, W. P., Dependence on pH of the Activity of Pig Liver Esterase. Arch. Biophy. 203, 227-35 (1980); and Guanti, G., Banfi, L., Narisano, E., Riva, R. and Thea, S., Enzymes in Asymmetric Synthesis: Effect of Reaction Media on the PLE Catalyzed Hydrolysis of Diesters, Tet. Let. 27, 4639-4642 (1986). Depending on the substrate, each of these isozymes may react differently to changes in the reaction conditions, and may give differing stereospecificity. However, no indication of isozyme existence in *C. rugosa* lipase exists, despite the fact that the enzyme has been extensively investigated even with isoelectric focusing. See Gerlach, D., Schneider, S., Gollner, T., Kim, K. S., and Schreier, P., Screening of Lipases for Enantiomer Resolution of Secondary Alcohols by Esterification in Organic Medium, Bioflavour '87, Proc. Int. Conf., 1988 Walter de Gruyter & Co., Berlin.

Notwithstanding the foregoing prior efforts, there is still considerable room for providing improved procedures for stereoselectively hydrolyzing or transesterifying esters or for esterifying alcohols or esters by enzymatic means. For example, there is a continuing interest in the enzymatic hydrolysis of (R,S)-(+)-methyl-2-(4-hydroxyphenoxy)-propionate (HPPA-Me) to produce (R)-HPPA in greater than 95% ee. Racemic HPPA is a valuable intermediate in the production of certain herbicides. Over 95% of he herbicidal activity of quizalofop ethyl has been found to lie in the (R)-isomer which is conveniently synthesized from (R)-HPPA. It, therefore, is of considerable significance to be able to resolve the racemic ester of HPPA in an economic fashion to provide this intermediate on an industrial scale. A purpose of the invention is to provide such improvements in enzymatic hydrolysis, esterification and transesterification procedures. Other objects will also be hereinafter evident.

SUMMARY OF THE INVENTION

The present invention provides processes for stereoselectively hydrolyzing racemic mixtures of esters of 2-substituted acids with certain lipase preparations of Candida rugosa in aqueous/organic systems, where the acid is not substituted at the 2-position with a halogen. These processes are highly stereoselective for the hydrolysis. The invention also contemplates processes involving the transesterification of various esters and the esterification of acids and alcohols. The present invention also includes a process for the production of R-2-(4-hydroxyphenoxy)propionic acid at high enantiomeric excess using an enzyme. The invention also includes two highly useful isozymes discovered to be present in lipase preparations of *Candida rugosa* and a process for separating and purifying these isozymes from the lipase of *Candida rugosa* by chromatography as well as by isoelectric focusing. The use of these isozymes for hydrolysis of esters, transesterification of esters and esterification of acids is another feature of the invention. In addition, the use of these isozymes to stereoselectively hydrolyze, esterify or transesterify is given. Methods of immobilization are disclosed and, the use of the immobilized isozymes as well as the immobilized lipase of *Candida rugosa* are provided. A method for purification of enzyme activity by immobilization is also given. Additionally, a method is disclosed for the use of reducing agents to stabilize enzymatic hydrolyses. The use of the enzymes, isozymes and immobilized forms thereof in the presence of organic solvents is also described. Processes for the stereoselective production of 2-aryloxy substituted acids are given and the production of R-2-(4-hydroxyphenoxy)propionic acid is described using isozymes. The stereoselective production by isozymes of 2-arylpropionic acids is described and processes for the production of S-ketoprofen, S-ibuprofen, S-fenoprofen, S-2-phenylpropionic acid and S-indoprofen by this route are also provided. Also provided is a method for increasing the rate or stereoselectivity of a lipase mediated reaction.

According to one aspect of the invention there is provided a process for stereoselectively hydrolyzing esters into acids at high enantiomeric excess with either free or immobilized enzymes in a two-phase aqueous organic system where the organic phase is an aromatic organic solvent and where the two position of the acid is not substituted by a halogen.

According to another aspect of the invention, there is provided a process for production of R-2-(4-hydroxyphenoxy)propionic acid with enzymes from *Candida rugosa*.

Other aspects of the invention include the following:
(1) a process for improving the stability of an enzyme or isozyme, used in the production of 2-(4-hydroxyphenoxy) propionic acid, with the use of a reducing agent;
(2) a process for purifying and separating isozymes from preparations of the lipase of *Candida rugosa*, which comprises using ion exchange chromatography with an appropriate elution scheme to separate the lipase isozymes;
(3) a process for purifying and separating isozymes of the lipase from *Candida rugosa* using isoelectric focusing;
(4) an isolated isozyme of the lipase of *Candida rugosa* having an N terminal amino acid sequence:

Ala—Pro—Thr—Ala—U—Leu—Ala—Asn—Gly—V—
Thr—Ile—Thr—Gly—Leu—Asn—Ala—Ile—Ile—Asn—
Glu—Ala—Phe—Leu—Gly—Ile—W—X—Ala—Glu—
Pro—Pro—Y—Z—Asn—P wherein U, V, W, X, Y and Z are amino acids and P is the remaining portion of the peptide. More specifically and further in accordance with the invention, there is provided an isolated isozyme, referred to as CSC-1, and having the N terminal amino acid sequence:

Ala—Pro—Thr—Ala—Lys—Leu—Ala—Asn—Gly—V—
Thr—Ile—Thr—Gly—Leu—Asn—Ala—Ile—Ile—Asn—
Glu—Ala—Phe—Leu—Gly—Ile—Pro—Phe—Ala—Glu—
Pro—Pro—Val—Gly—Asn—P wherein V is an amino acid and P is the remaining portion of the peptide. Also according to the invention, there is provided an isolated isozyme, referred to as CSC-2, and having the N terminal amino acid sequence:

Ala—Pro—Thr—Ala—Thr—Leu—Ala—Asn—Gly—Asp—
Thr—Ile—Thr—Gly—Leu—Asn—Ala—Ile—Ile—Asn—
Glu—Ala—Phe—Leu—Gly—Ile—W—X—Ala—Glu—
Pro—Pro—Y—Z—Asn—Leu—Phe—Ile—ZZ—Leu—P wherein W, X, Y, Z, and ZZ are amino acids and P is the remaining portion of the peptide.

It will be evident to one skilled in the art that the isozymes described above can be obtained by methods involving recombinant DNA, wherein other methods of isolation might become possible. It is also apparent that minor amino acid sequence changes in the structure of the isozymes described above may be carried out by methods involving recombinant DNA without affecting the nature of the action and specificity of the isozymes while changing the amino acid sequence as given above;

(5) a process for hydrolyzing esters in the presence of a lipase isozyme;

(6) a process for esterifying acids or alcohols in the presence of a lipase isozyme;

(7) a process for transesterifying esters in the presence of a lipase isozyme;

(8) a process for stereoselectively hydrolyzing esters in the presence of a lipase isozyme;

(9) a process for stereoselectively esterifying acids or alcohols in the presence of a lipase isozyme;

(10) a process for stereoselectively transesterifying esters in the presence of a lipase isozyme;

(11) processes for immobilizing the enzymes and isozymes of the lipase of *Candida rugosa;*

(12) processes for using the immobilized enzymes and immobilized isozymes of the lipase of *Candida rugosa;*

(13) a process for purification of an enzyme by immobilization;

(14) processes for using the enzymes, isozymes or immobilized enzymes or immobilized isozymes in two phase aqueous/organic systems;

(15) a process for the production of specific enantiomers of 2-aryloxy substituted acids with lipase isozymes;

(16) a process for the production of R-2-(4-hydroxyphenoxy) propionic acid with lipase isozymes;

(17) a process for the resolution of 2-arylpropionic acids with lipase isozymes. Specifically, there are included processes for the production of S-ketoprofen, S-ibuprofen, S-fenoprofen, S-2-phenylpropionic acid and S-indoprofen. These processes are especially valuable with certain esters which are disclosed; and

(18) the use of certain additives which enhance the rate or stereoselectivity of the *Candida rugosa* lipase or the isozymes of *Candida rugosa.*

Additional features, objects and advantages of the invention are set forth in the more detailed description which follows.

DESCRIPTION OF THE PREFERRED EMBODIMENTS

Figure 1:
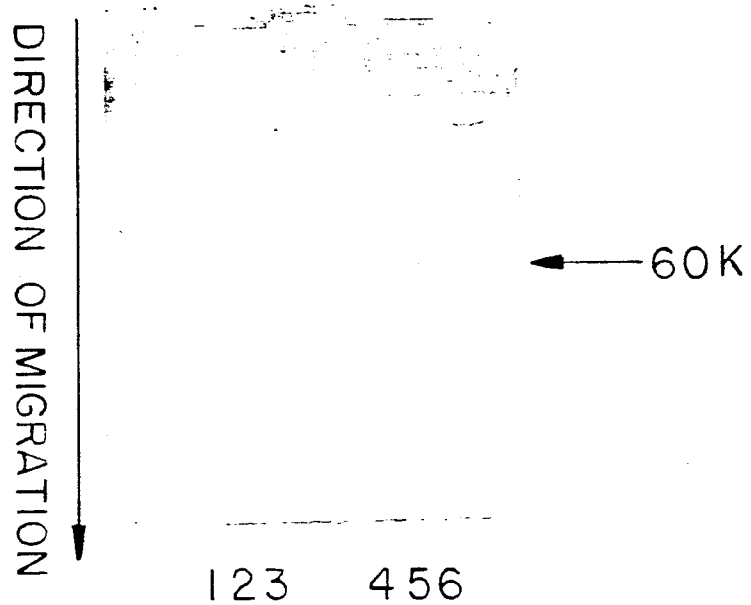

The present invention includes a process for stereoselectively hydrolyzing racemic mixtures of esters into acids. This process comprises the steps of:

a) immobilizing the lipase enzyme or an isozyme of *Candida rugosa;* and b) contacting the immobilized enzyme or isozyme with a racemic mixture of esters in the presence of an organic solvent which increases the stereoselectivity of the process. Organic solvents that optimize the stereoselectivity of the process include aromatic organic solvents, especially aromatic hydrocarbons. An especially preferred organic solvent is toluene. See Example 6. However, other organic solvents may also be used. This includes without limitation halogenated hydrocarbons.

Reaction conditions, e.g. temperature and time, may be varied. Advantageously room temperature (20°-25° C.) is used although other temperatures are also useful. Optimum reaction times, pH and other conditions can be readily determined for any specific situation.

Preferred esters that can be stereospecifically hydrolyzed in accordance with the claimed invention using the lipase enzyme or isozymes of *Candida rugosa* are the esters of 2-(aryloxy)propionic acids, particularly 2-(4-hydroxyphenoxy)propionic acid (hereinafter sometimes referred to as "HPPA"). The stereoselectivity increases when the enzyme is immobilized, preferably by using a polyaziridine prepolymer. Reducing agents e.g. sodium hydrosulfite, can be added, in small amounts to prevent the oxidation of HPPA and its esters.

As shown in Example 9, the stereospecificity of the immobilized enzyme increases with usage. In the first batch hydrolysis of HPPA-Me to HPPA resulted in the production of 82% R-HPPA and 18% S-HPPA, whereas in both the seventh and eighth batch hydrolyses, the conversion was 100% R-HPPA and 0% S-HPPA. Although the stereospecificity significantly increased with usage, the activity slightly decreased. The increased stereospecificity obtained in accordance with the claimed process is critical for an industrial process since as noted earlier, an industrial process normally requires greater than 95% ee.

The invention also includes a process for purifying and separating stereoselective enzymes of the lipase of *Candida rugosa,* which comprises using ion exchange chromatography; and separating the resulting lipase isozymes with an appropriate elution scheme. The elution scheme can be either a stepwise pH scheme, a pH gradient scheme, or a salt elution scheme. A preferred elution scheme is the stepwise pH scheme. A preferred application of this process involves purifying the enzymes of the lipase of *Candida rugosa* so as to elute the two isozymes, CSC-1 and CSC-2.

The purification and separation of stereoselective isozymes of the lipase *Candida rugosa* may also be accomplished using isoelectric focusing. As demonstrated in Example 58 the enzyme of the lipase of *Candida rugosa* may be separated into two isozymes, CSC-1 and CSC-2, both of which demonstrate exceptional stereospecific hydrolytic activity.

The purification and separation process of the invention is suitable for use on a large scale. Various chromatography supports can be used in the present invention. Preferably, the chromatography support is substituted with a strong acid. More specifically, the chromatography support is derivatized with a sulfopropyl functional group. Preferred supports include SP-Trisacryl ™, and SP-Sephacryl ™. See Examples 11, 12, 13, and 14.

As noted earlier, the invention provides an isolated isozyme of the lipase of *Candida rugosa* having the N terminal amino acid sequence:

Ala—Pro—Thr—Ala—U—Leu—Ala—Asn—Gly—V—
Thr—Ile—Thr—Gly—Leu—Asn—Ala—Ile—Ile—Asn—
Glu—Ala—Phe—Leu—Gly—Ile—W—X—Ala—Glu—

-continued
```
Pro—Pro—Y—Z—Asn—P
``` wherein U, V, W, X, Y and Z are amino acids and P is a peptide. More specifically, the invention contemplates such an isozyme, referred to as CSC-1, having the sequence:

```
Ala—Pro—Thr—Ala—Lys—Leu—Ala—Asn—Gly—V—
Thr—Ile—Thr—Gly—Leu—Asn—Ala—Ile—Ile—Asn—
Glu—Ala—Phe—Leu—Gly—Ile—Pro—Phe—Ala—Glu—
Pro—Pro—Val—Gly—Asn—P
``` wherein V is an amino acid and P is a peptide the remaining portion of the peptide. CSC-1 is also characterized by an isoelectric point of 5.3-5.7 and a molecular weight of 55-65000.

The invention also provides another isozyme isolated from the lipase of *Candida rugosa*, referred to as CSC-2, and having an N terminal amino acid sequence:

```
Ala—Pro—Thr—Ala—Thr—Leu—Ala—Asn—Gly—Asp—
Thr—Ile—Thr—Gly—Leu—Asn—Ala—Ile—Ile—Asn—
Glu—Ala—Phe—Leu—Gly—Ile—W—X—Ala—Glu—
Pro—Pro—Y—Z—Asn—Leu—Phe—Ile—ZZ—Leu—P
``` wherein W, X, Y, Z, and ZZ are amino acids and P is the remaining portion of the peptide.

It has been found that the isozymes CSC-1 and CSC-2, obtained from the lipase of *Candida rugosa*, have different and sometimes opposing stereoselectivities. These isozymes, CSC-1 and CSC-2, are useful in the stereoselective hydrolysis of various esters, as described below.

The lipase of *Candida rugosa* which is used herein either as such or for isolation of the indicated isozymes, is available from several commercial sources. While the commercially available enzymes are all derived from *Candida rugosa*, they differ in isoelectric focusing profile and they also exhibit a large variation in the concentration of the proteins which are present. It has also been found that the commercial enzyme preparations demonstrate varying degrees of stereospecificity for hydrolysis of esters. The reason for the differences in the stereospecificity of hydrolysis of the commercially available lipases is apparently due to the variation in the concentration of several proteins present in the lipase of *Candida rugosa*. While the isozymes CSC-1 and CSC-2 may be present in all available lipase of *Candida rugosa*, certain of such lipase preparations are preferred as sources for the isozymes. Lipase MY from Meito Sangyo is advantageously used in the isolation of the isozymes, CSC-1 and CSC-2. Other lipases, such as Lipase AY and Lipase Sigma, are also suitable.

Samples of both CSC-1 and CSC-2 have been analyzed by microsequencing techniques. The microsequencing shows the two fractions are in fact different enzymes and not degraded products of each other. See Example 13. Microsequencing also shows that there is large sequence homology between CSC-1 and an acetylcholine esterase from *Torpedo californica*, the electric eel. However, upon checking the eel acetylcholine esterase for its ability to hydrolyze HPPA esters, very low hydrolyzing activity with no stereospecificity was seen. See Example 13.

This serves to underscore the unobviousness in finding that the isozymes are uniquely effective in their stereospecificity activity. The composition of the two novel isozymes, CSC-1 and CSC-2, is illustrated by their N-terminal amino acid sequence, noted earlier and as shown in Example 13.

It has been found according to the invention that the isozymes, CSC-1 and CSC-2, when used in the hydrolysis of a racemic mixture of esters produce highly chiral products. The isozyme CSC-1 has been shown to give highly stereoselective hydrolysis of racemic mixtures of the methyl or ethyl esters of 2-(4-hydroxyphenoxy)propionic acid. See Examples 15 and 16. The isozyme CSC-2 is particularly effective at stereoselectively hydrolyzing esters of ketoprofen Hydrolysis of esters using CSC-1 and CSC-2 can be conducted using a two-phase (aqueous/organic) reaction medium.

The activities of CSC-1 and CSC-2 vary significantly and one may be preferred over the other for any particular reaction. For example a comparison of CSC-1 and CSC-2 shows that the rate of conversion of racemic HPPA methyl ester is far higher for CSC-1 than for CSC-2 and that the enantiomeric excess was also slightly increased. See Example 17. On the other hand, superior results are obtained when the esters of ketoprofen are hydrolyzed with CSC-2. The isozyme CSC-2 is also superior to lipase MY for hydrolysis of esters of ketoprofen and the rate for CSC-2 hydrolysis is also significantly better than that of lipase MY, although the lipase itself may be used. See Example 18 and 19. The use of a two-phase mixture in isooctane or like solvent (preferably hydrocarbon) also gives excellent enantiomeric excess (ee). See Example 18. A comparison of the effect of CSC-1, CSC-2 and Lipase MY indicates the superiority of CSC-2 for hydrolysis of ketoprofen monoglyceride in addition to its superior enantiomeric excess. See Example 19.

Organic solvents may be advantageously used to increase the solubility of ketoprofen methyl esters in water which is usually buffered to give a pH of around 6-8. However, care needs to be taken to insure that the solvent used, or the amount thereof, does not affect the results. Thus, for example, it has been found that the dissolution of ketoprofen esters in dimethylformamide (DMF) with increasing quantities of DMF may have a deleterious effect on the CSC-2 isozyme. The large scale hydrolysis of ketoprofen monoglyceride may also show a low enantiomeric excess when a substantial amount of DMF is added. See Examples 20 and 21.

In accordance with another aspect of the invention, the hydrolysis of esters with CSC-2 can be conducted in the presence of a surfactant. An advantage in using an additive such as a surfactant, is that any adverse effect of DMF on ee can be prevented or minimized. See Example 22. Preferred surfactant additives include oleate esters, vegetable oils, animal oils and other oleate containing surfactants.

The use of low polarity solvents in a two-phase system for the hydrolysis of ketoprofen monoglyceride is also advantageous in providing superior rates and ee. See Example 23.

The isozymes or lipase can be usefully immobilized in a large variety of ways, all of which provide active material. The immobilized isozymes can then be used in producing chiral acids. For example, the isozyme CSC-1 can be immobilized and used in the hydrolysis of various esters. Immobilization of the isozyme CSC-1 using polyaziridine or Eupergit C is highly effective for the hydrolysis. See Example 25. Example 33 shows that there is an extended catalyst lifetime for CSC-1 immobilized by the polyaziridine procedure. The immobilization can be undertaken in the presence of an organic acid. See Example 29. It has also been found that polyvinyl alcohol has a beneficial effect on the immobilization of lipase CSC-1 as the relative activity appears to be substantially increased by the addition of this reagent. See Example 30.

A preferred method of immobilization for the isozyme CSC-2 involves the use of silica. See Example 24. Example 31 illustrates immobilization of crude Lipase MY.

Organic acids also appear to have a positive effect on the immobilization as demonstrated with Lipase MY in Example 26. Although each of the acids tested is shown to be somewhat effective, it appears that preferred acids are those having 12-18 carbon atoms, stearic acid being preferred. The effect of stearic acid is dose related below 5% concentration whereas above this level there is a consistent effect for the immobilization. See Example 27. A finer delineation of the protective effect of stearic acid indicates that 5% stearic acid is optimum for the relative activity. However, other dosages are effective and may be used. See Example 28.

An alternative method for the production of the stereospecific lipases shows that both cation and anion exchangers can be used for the isolation of CSC-1. See Example 34.

The isozymes CSC-1 and CSC-2, are effective in hydrolyzing esters of 2-arylpropionic acids such as ibuprofen esters, fenoprofen methyl ester, 2-phenylpropionic acid methyl ester, and indoprofen monoglyceride by way of illustration. As shown in Example 35, ibuprofen, a non-steroidal, anti-flammatory, is resolved effectively by Lipase MY, CSC-2 and CSC-1, the rates and ee being highest with CSC-2. For fenoprofen methyl ester, another non-steroidal anti-inflammatory, CSC-1 and CSC-2 have clearly superior rates and stereoselectivities. See Example 36.

The effective rate of hydrolysis of the methyl esters of ketoprofen and ibuprofen appears to be superior for CSC-2; however, CSC-2 and CSC-1 are equal in rate for fenoprofen. See Example 36. Example 37 shows the use of CSC-1 and CSC-2 for the resolution of 2-phenylpropionic acid methyl ester. Again, CSC-2 predominates in rate and stereoselectivity although both isozymes are superior to Lipase MY, even though Lipase MY is used in much greater quantity.

The hydrolysis of indoprofen monoglyceride shows that CSC-2 gives a stereospecific resolution in which the S-form predominates while Lipase MY and CSC-1 give predominantly the R-form. See Example 38.

The use of a surfactant in the hydrolysis of ketoprofen monoglyceride by CSC-2 resulted in an increase in the relative rate. For instance, Tween 80 is effective when added to the reaction mix in the presence or absence of BSA. See Example 39. This effect was examined further for a large number of surfactants of various types. It can be seen from Example 40 that the major accelerators of enzyme rate for CSC-2 are the oleic acid esters. Oleate esters, specifically, were evaluated and it was found that the percent ee and the rate of hydrolysis were increased for CSC-2 on ketoprofen monoglyceride. See Example 41. Other oleic acid derivatives which are not generally used as surfactants were evaluated and it was shown that oleic acid and its esters increased the rate as well as the enantioselectivity. See Example 42.

Oleate esters are also found in natural oils. Thus, natural oils were also tested for their effect on hydrolysis. Olive oil shows a specific stimulation of CSC-2 activity. See Example 43. It was also shown that olive oil and corn oil act as natural substrates for hydrolysis using CSC-2 and that transesterification also occurs. See Example 44. Thus, transesterifications may increase the value of low grade or undesirable oils which have or one might wish would have oleic esters. The isozymes of the present invention may also be used to hydrolyze such oils which are of low grade to produce valuable acids which may be separated by known chemical methods. See Example 44. Other naturally occurring triglycerides have also been evaluated. See Example 45. The natural oils tested, which were glycerol esters, were found to be accelerators of CSC-2 activity. Example 46 shows that the addition of a number of oleic esters or oleate acid will increase the rate and the enantiospecificity of the hydrolysis of esters ketoprofen by CSC-2 and also indicates the extraction procedure used must be such that it will separate the oil/oleic acid from the ketoprofen. See Example 46.

However, not all oils enhance the activity of CSC-2 with all substrates. For example, mineral oil, a mixed hydrocarbon, did not accelerate the hydrolysis of ketoprofen monoglyceride. See Example 47. It was further found on examination of esters, other than those of oleic acid and linoleic methyl ester that no rate enhancement occurred. See Example 48.

Oleic acid was found to have a rate enhancing effect on both lipase MY and CSC-2, but not on CSC-1. Oleic acid also increased the enantiomeric excess for CSC-2, but not as dramatically for lipase MY. See Example 49. Oleic acid was found to be effective in promoting the hydrolysis of hydroxy esters ketoprofen. The oleic acid effect was seen on both Lipase MY and the Biocatalyst lipase B. See Example 50. A notable improvement in the hydrolysis of the 2-chloroethyl ester of ketoprofen was seen for CSC-2 and lipase MY in the presence of oleic acid and again the ee was increased. See Example 51.

A survey of hydrolyses with other enzymes with oleic acids/esters and a comparison of the effect on rate enhancement and ee shows that lipase OF and Biocatalyst Candida lipase give dramatic increases with hydroxy esters. Pig liver esterase hydrolyzed these hydroxy esters to give the opposite enantiomer. See Example 52. The use of immobilized CSC-2 showed the same type of rate enhancement and enantiomeric excess as that for the free CSC-2 when oleic acid was added. See Example 53.

The addition of an organic solvent such as hexane also shows significant rate enhancement when increasing concentrations of oleic acid are present. A concentration of 1 to 25% oleic acid in hexane, volume to volume, is useful. The preferred range is 5 to 15%. See Example 54 and 56. Examination of additional solvents showed that neither aromatic solvents (toluene) nor chlorinated solvents (chloroform) were as beneficial. However, aliphatic solvents such as hexane and isooctane gave significantly increased rates. See Example 55. A further examination of additional solvents with both ketoprofen monoglyceride (KPG) and ketoprofen ethylene glycol (KPEG) esters showed that aliphatic solvents gave improvements in rate and in enantiomeric excess. See Example 56.

A *C. rugosa* lipase Enzeco Rxx, which appeared to be the same as CSC-2 by IEF, had a slightly higher molecular weight and gave quite different stereoselectivity. Unusually, a rate enhancement with oleic acid was seen in the hydrolysis of KPEG, but not KPG. This indicates that either SDS-PAGE or IEF alone is not enough to distinguish the different enzymes. See example 57.

The enzyme preparation of Lipase MY may also be separated on a preparative scale by isoelectric focusing and CSC-1 and CSC-2 may be obtained in this manner. See example 58.

Suitable methods for immobilizing the lipase for use herein are known in the art. See, for example, U.S. Pat. No. 4,436,813 which describes the immobilization of enzymes or cells containing the same using prepolymer materials such as polyazetidine prepolymers (e.g. Polycup), carboxymethyl cellulose, polymethylene isocyanate and polyurethane hydrogel prepolymers. Any of these materials may be used for present purposes in the manner described in 4,436,813. Also useful herein for immobilizing the enzyme are curable, polyfunctional aziridine prepolymers as described in U.S. Patent 4,650,755 and Serial No. 938,248, the contents of which are incorporated herein by reference. Additional immobilizing agents are illustrated in the examples given herein.

The following examples illustrate, but do not limit, the invention:

EXAMPLE 1

The proteins present in commercial *C. rugosa* lipases from three available sources (Meito Sangyo, Biocatalyst Ltd., and Amano) were examined by SDS-PAGE to determine molecular weight profiles. Enzyme preparations were dissolved in 1% SDS- .05M Tris pH 8.0, 1% mercaptoethanol at a concentration of 1 mg/ml. The samples were analyzed on a Phast system (Pharmacia LKB) using pre-made 10-15% gradient polyacrylamide gels. Protein (0.2ug-2.0ug/lane) was applied to the gel and run for 73 volt-hr at 15° C. Gels were fixed in ethanol-acetic acid and the protein was stained with silver using the Pharmacia development chamber.

Lipase MY (Meito Sangyo), Lipase AY (Amano) and Candida cylindracea lipase (Biocatalyst) each had one major band on the gel with a molecular weight of 60 kilodaltons, (see FIG. 1). However, as also shown in FIG. 1, Lipase AY (Lanes 2 and 5) had another major band.

EXAMPLE 2

The composition of commercially available lipase MY was examined using CM-Trisacryl and DEAE-Trisacryl chromatography.

Lipase MY (Meito Sangyo), 0.33gm was dissolved in 10ml of 0.25mM $Na_2HPO_4$ (pH 7.0), and solids were removed by centrifugation. The protein was applied to a 2.5×10cm CM-Trisacryl M column equilibrated in the same buffer. The flow rate was adjusted to 1.0ml/min. The resin was washed with the same buffer until the absorbance at 280nm was zero. A single protein peak containing all the enzymatic activity was eluted using this ion exchange resin.

Lipase MY, 5gm, was dissolved in 0.15M NaCl -0.01M $Na_2HPO_4$ (pH 7.3), and the solids were removed by centrifugation. The protein was desalted by chromatography on Sephadex G-25 resin with 25mM $Na_2HPO_4$ (pH 7.0). The protein fractions were pooled and applied to a DEAE-TrisAcryl M column 2.5×10cm equilibrated in 25mM $Na_2HPO_4$ pH 7.0. Elution was carried out by washing the resin with the same buffer. All enzyme activity and protein eluted as a single peak. Based on this data it is assumed that the protein in the Lipase MY preparation is a single species.

EXAMPLE 3

This example illustrates the hydrolysis of the methyl ester of 2-(4-hydroxyphenoxy) propionic acid (HPPA-Me) using Lipase MY.

Lipase MY (Meito Sangyo), 340mg, 4g of R,S-HPPA methyl ester, and 200ml of 20mM $KH_2PO_4$ (adjusted to pH 6.5) were mixed, with shaking, for 5.5 hours.

Analysis of the acid formed was carried out by extraction of the ester after adjustment of the aqueous solution to pH 6.5 (a slight pH drop occurs on hydrolysis) with $CH_2Cl_2$ followed by adjusting the pH to 2 and extraction of the acid with ethyl acetate. The solution was evaporated to dryness, taken up in water and analyzed by HPLC with a Macherey Nagel-Duren Resolvosil BSA- column using 5% n-propanol, 10mM $KH_2PO_4$, pH 5 at 2.7ml/min with detection at 220nm. At that time 35% of the R, S-ester was converted to the acid. The ratio of R and S acids was 94% R and 6% S.

EXAMPLE 4

Comparison of the stereoselectivity of commercially available lipases obtained from *C. rugosa*.

Lipase MY (Meito Sangyo), Candida lipase B (Biocatalyst, Ltd), lipase OF (Meito Sangyo), and Lipase AY (Amano) were compared for stereoselectivity for production of R-HPPA from R,S-HPPA methyl ester. The preparations, in amounts shown in Table I, were added to 50 ml of 20 mM HPPA methyl ester in 50 mM $KH_2PO_4$ pH 6.5. The substrate lipase reactions were incubated with shaking at 25° C. for up to 22 hours. The ratio of R to S acid was determined by HPLC as described in Example 3 at approximately 16% hydrolysis of the ester. The results are shown in Table 1:

TABLE 1

| Lipase preparation | mg of enzyme added | % R-acid |
| --- | --- | --- |
| Lipase MY | 10.7 | 93 |
| Lipase AY | 10.6 | 93 |
| Lipase B | 9.4 | 69 |
| Lipase OF | 9.6 | 68 |

As indicated, Lipase MY and Lipase AY both demonstrated greater stereospecificity than lipase B or lipase OF.

EXAMPLE 5

This example describes the two phase lipase MY hydrolysis of HPPA-Me.

Soluble Lipase MY enzyme (2gm) was added to toluene (50ml) containing 1M HPPA-Me (196 gm/l) and 50ml 1M $KH_2PO_4$ pH 7.0 and allowed to convert the R,S ester to the acid. The acid ratio in this two-phase system (toluene/water), at 46% hydrolysis of the R,S ester, was 92% R-acid and 8% S-acid.

EXAMPLE 6

Optimization of two phase Lipase MY hydrolysis in various organic solvent/water mixtures.

All reactions were set-up as follows:

A. 75% organic solvent/25% aqueous buffer—Fifty milligrams of R,S-HPPA-Me was combined in 10 ml Scintillation vial with 7.5 ml of organic solvent, 2.5 ml of 50 mM phosphate buffer pH 6.0, and 5 mg Lipase MY. The reactions were placed on shaker and shaken for a period of 0–43 hours with samples being taken at various times.

B. 25% organic solvent/75% aqueous buffer—Fifty milligrams of R,S-HPPA-Me was combined, in 10 ml Scintillation vial with 2.5 ml of organic solvent, 7.5 ml 50mM phosphate buffer (pH 6.8), and 5 mg Lipase MY. The reactions were shaken for a period of 0-143 hours with samples being taken at various time points.

The data in Table 2 represents the % conversion and % R-HPPA produced using the indicated organic solvents in a two-phase system wherein 75% dry volume of the total vehicle (solvent) was water and the balance (25%) was organic solvents.

TABLE 2

| Solvent | Solvent % | Time (Hr) | Conversion (ester/acid) | % R % | Solubility (HPPA-ME) mg/ml |
|---|---|---|---|---|---|
| carbon tetrachloride | 25 | 2.7 | 58 | 79 | 33.0 |
|  | 75 | 2.7 | 61 | 76 |  |
| 1,2-dibromoethane | 25 | 43 | 33 | 73 | 565.7 |
|  | 75 | 43 | 23 | 57 |  |
| tetrachloroethylene | 25 | 5.3 | 61 | 83 | 1.4 |
|  | 75 | 5.3 | 58 | 85 |  |
| 1,1,2 trichloroethane | 25 | 43 | 29 | 79 | 558.0 |
| trichlorotrifluoroethane | 25 | 5.3 | 49 | 100 | insoluble |
|  | 75 | 2.7 | 60 | 85 |  |
| xylenes | 25 | 5.3 | 49 | 100 |  |
|  | 75 | 5.36 | 41 | 89 |  |
| toluene | 25 | 2.7 | 385 | 100 | 236.3 |
|  | 75 | 2.7 | 25 | 90 |  |
| acetone | 25 | 43 | 0 | 0 | nt |
|  | 75 | 43 | 0 | 0 | nt |
| 2-propanol | 25 | 43 | 0 | 0 | nt |
|  | 75 | 43 | 0 | 0 | nt |
| cumene | 25 | 2.7 | 35 | 100 | 20.0 |
| cyclohexane | 25 | 2.7 | 35 | 100 | 66.4 |
|  | 75 | 2.7 | 31 | 83 |  |
| fluorobenzene | 25 | 5.3 | 40 | 95 | 155.5 |
|  | 75 | 5.3 | 29 | 86 |  |
| ethyl alcohol | 25 | 43 | 0 | 0 | nt |
|  | 75 | 43 | 0 | 0 | nt |

As will be seen the best results were obtained using the lower amount of solvent with the aryl hydrocarbons or mixed chlorofluorohydrocarbon, namely trichlorotrifluoroethane.

EXAMPLE 7

This example illustrates the use of immobilized lipase MY in the hydrolysis of HPPA-Me.

Immobilized lipase MY as prepared by the following methods was shaken with a toluene solution of HPPA-Me and phosphate buffer (pH 6.5) at room temperature for up to 60 hrs. The aqueous solution was then assayed for the concentration of R-HPPA by HPLC as in Example 3. The enzyme was washed with deionized water and added to a new batch.

A. Immobilization of Lipase MY on Amberlite IRC-84 or DP-1 with XAMA-7. Lipase MY (1.10g) was mixed thoroughly with 2.5g of dehydrated Amberlite IRC-84, or Amberlite DP-1 0.85g of XAMA-7 and 2ml of phosphate buffer (pH 6.5, 0.1M). The mixture was allowed to stand at room temperature for 4 hrs during which time the enzyme was immobilized. The catalyst was washed and then stored at 4° C.

B. Immobilization of Lipase MY on Amberlite DP-1 with Polycup. Lipase MY 0.15g, dehydrated Amberlite DP-1 0.5g and Polycup 2ml were heated at 45° C. for 4 hrs. The immobilized enzyme was washed and assayed with HPPA-Me. The immobilization yield was 40%.

C. Immobilization of Lipase MY on Sodium Periodate Activated Cellulose Beads. Lipase MY 0.15g and sodium periodate (NaIO$_4$) activated cellulose beads 1g were shaken in 5ml of phosphate buffered saline (PBS) at room temperature for 20 hrs. The immobilized enzyme was collected, washed and assayed with HPPA-Me. The immobilization yield was 90%.

D. Immobilization of Lipase MY on Chitin with Glutaraldehyde. Lipase MY 0.25g, chitin 0.5g and glutaraldehyde (50%) 500ul were shaken in 10ml of PBS at room temperature for 20 hrs. The immobilized enzyme was collected, washed and tested with HPPA-Me. The immobilization yield was 67%.

E. Immobilization of Lipase MY on Hexanediamine - Cellulose Beads with Glutaraldehyde. Lipase MY 0.25g, hexanediamine-cellulose beads 1g and glutaraldehyde (50%) 500ul were shaken in 5ml of PBS at room temperature for 20 hrs. The immobilized enzyme was collected, washed and assayed with HPPA-Me. The immobilization yield was 54%.

F. Immobilization of Lipase MY on Polyethyleneimine (PEI)- Cellulose Beads with glutaraldehyde. Preparation of the PEI-cellulose beads consisted of mixing dehydrated cellulose beads 10g, PEI (50%) 3g, cyanuric chloride 2g and triethylamine, 2.5ml, in 20ml of acetonitrile at 40° C. for 15 hrs. The beads were then collected and washed with 200ml each of 0.01 N HCl, methanol, 0.05 N NaOH, methanol and deionized water. Lipase MY (0.25g) was immobilized by shaking PEI-cellulose beads 2g and glutaraldehyde (50%) 500ul in 10ml of PBS at room temperature for 24 hrs. The immobilized enzyme was collected, washed and assayed with HPPA-Me. The immobilization yield was 71%.

G. Immobilization of Lipase MY on PEI-Cellulose Beads with Carbodiimide. Lipase MY 0.25g, PEI-cellulose beads (from F above) 1g and carbodiimide 0.25g were shaken in 10ml of PBS at 4° C. for 65 hrs. The immobilized enzyme was collected, washed and assayed with HPPA-Me. The immobilization yield was 34%.

H. Immobilization of Lipase MY on PEI-Cellulose Beads (from F above) with Toluene-2,4 Diisocyanate. Lipase MY 0.25g, PEI-cellulose beads 1g and toluene 2,4-diisocyanate (10mg) were shaken in 5ml of PBS at RT for 20 hrs. The immobilized enzyme was collected, washed and assayed with HPPA-Me. The immobilization yield was 4.4%.

EXAMPLE 8

This example illustrates the effect of reducing agents towards stabilizing lipase in the presence of HPPA.

The asymmetric hydrolysis of HPPA-Me was conducted in the biphasic aqueous-organic system used in Example 5. The ester was predominantly in the organic phase while the enzyme and the acid were predominantly in the aqueous phase.

The effect of sodium hydrosulfite (Table 3), sodium sulfite (Table 4), cystine (Table 5) and various reducing agents (Table 6) was evaluated. Sodium hydrosulfite was effective at preventing loss of enzyme activity. Neither sodium sulfite nor cystine was effective at preventing loss of enzyme activity.

Lipase MY 5.0g was immobilized on 10g of Amberlite DP-1 with 2.5g of XAMA-7. The immobilized enzyme 0.89g (eq. 150 mg crude enzyme) was shaken with 2.5 ml of 1M HPPA (phosphate, pH 6.5) containing 2, 4, 8 and 16 mg/ml of reducing reagents for 4 days. Cystine, sodium hypophosphite, tetrabutylammonium borohydride, tetrabutylammonium cyanoborohydride, sodium sulfite and sodium hydrosulfite were tested. The immobilized enzyme was then washed with deionized water and assayed with HPPA-Me. The untreated immobilized enzyme was used as a control to calculate the residual activity of the HPPA treated enzyme. The HPPA treated lipase retained 70% of the activity when no reducing reagents were employed.

TABLE 3

| Batch # | Reaction Time (hrs) | HPPA-Me Conc. (mMole) | $Na_2S_2O_4$ (mg) | | | | | |
|---|---|---|---|---|---|---|---|---|
| | | | 0 | 2.5 | 5 | 10 | 25 | 50 |
| | | Conversion (%) of HPPA-Me to HPPA | | | | | | |
| 1 | 15 | 10 | 33 | 37 | 36 | 30 | 25 | 24 |
| 3 | 15 | 10 | 25 | 29 | 29 | 21 | 21 | 17 |
| 7 | 15 | 10 | 20 | 30 | 27 | 25 | 25 | 25 |
| 11 | 15 | 10 | 13 | 21 | 24 | 31 | 34 | 33 |
| 14 | 15 | 10 | 19 | 21 | 22 | 21 | 23 | 23 |
| 18 | 15 | 10 | 18 | 16 | 17 | 19 | 29 | 33 |
| 22 | 15 | 10 | 12 | 14 | 13 | 13 | 18 | 23 |
| 30 | 15 | 10 | 13 | 17 | 17 | 17 | 31 | 38 |

(1) Lipase MY 180 mg was immobilized on 2 ml of IRC-84 with 90 mg of XAMA-7 by the procedure in Example 7A.
(2) HPPA-Me/Toluene = 1 M/10 ml, pH 7 phosphate buffer 0.25 M × 20 ml.

TABLE 4

| Batch # | Reaction Time (hrs) | HPPA-Me Conc. (mMole) | $Na_2SO_3$ (mg) | | | | | |
|---|---|---|---|---|---|---|---|---|
| | | | 0 | 2.5 | 5 | 10 | 25 | 50 |
| | | Conversion (%) of HPPA-Me to HPPA | | | | | | |
| 3 | 15 | 10 | 28 | 39 | 20 | 26 | 32 | 25 |
| 7 | 15 | 10 | 13 | 17 | 14 | 20 | 17 | 25 |
| 9 | 15 | 10 | 13 | 14 | 11 | 16 | 13 | 18 |
| 12 | 15 | 10 | 14 | 16 | 12 | 14 | 12 | 18 |
| 14 | 15 | 10 | 13 | 13 | 9 | 13 | 10 | 16 |
| 18 | 15 | 10 | 16 | 14 | 10 | 14 | 12 | 12 |
| 19 | 15 | 10 | 13 | 13 | 11 | 15 | 12 | 13 |
| 20 | 15 | 10 | 14 | 14 | 10 | 14 | 11 | 14 |

(1) Lipase MY 200 mg was immobilized on 2 ml of IRC-84 with 100 mg of XAMA-7 by the procedure in Example 7 part A.
(2) HPPA-Me/Toluene = 1 M/10 ml, pH 7 phosphate buffer 0.25 M × 20 ml.

TABLE 5

| Batch # | Reaction Time (hrs) | HPPA-Me Conc. (mMole) | Cystine (mg) | | | | |
|---|---|---|---|---|---|---|---|
| | | | 0 | 2.5 | 5 | 10 | 25 |
| 1 | 15 | 10 | 36 | 30 | 34 | 35 | 36 |
| 5 | 15 | 10 | 27 | — | 31 | 28 | 26 |
| 9 | 15 | 10 | 14 | 19 | 11 | 16 | 16 |
| 15 | 15 | 10 | 17 | 19 | 17 | 16 | 17 |
| 16 | 15 | 10 | 19 | 17 | 16 | 15 | 13 |
| 20 | 15 | 10 | 19 | 16 | 16 | 17 | 16 |
| 21 | 15 | 10 | 15 | 20 | 18 | 15 | 17 |
| 22 | 15 | 10 | 17 | 20 | 17 | 17 | 17 |

(1) Lipase MY 240 mg was immobilized on 2 ml of IRC-84 with 120 mg XAMA-7 by the procedure given in Example 7 part A.
(2) HPPA-Me/Toluene = 1 M/10 ml, pH 7 phosphate buffer 0.25 M × 20 ml.

TABLE 6

| | Conc. (mg/ml) | Relative Activity (%) |
|---|---|---|
| cystine | 2 | 83 |
| | 4 | 76 |
| | 8 | 81 |
| | 16 | 83 |
| $NaH_2PO_2$ | 2 | 84 |
| | 4 | 81 |
| | 8 | 91 |
| | 16 | 91 |
| $Bu_4N\ CNBH_3$ | 2 | 83 |
| | 4 | 81 |
| | 8 | 88 |
| | 16 | 85 |
| $Bu_4N\ BH_4$ | 2 | — |
| | 4 | — |
| | 8 | 78 |
| | 16 | 79 |
| $Na_2SO_3$ | 2 | 95 |
| | 4 | 101 |
| | 8 | 110 |
| | 16 | 111 |
| $Na_2S_2O_4$ | 2 | — |
| | 4 | — |
| | 8 | 111 |
| | 16 | 112 |

Control Enzyme at 100%
HPPA Treated Enzyme at 70.4%

EXAMPLE 9

This example illustrates the increased enantioselectivity of immobilized lipase MY obtained with increased usage.

Twenty grams of crude Lipase MY (Meito Sangyo Ltd) were combined with 20ml of 25mM ammonium acetate buffer at pH 6.5 and stirred for 10 minutes. Ten grams of XAMA-7 polyaziridine pre-polymer (Cordova Chemical Co) were then slowly added and the mixture stirred for 1 minute. Forty grams of Amberlite DP-1 ion exchange resin (Rohm-Haas) were added to the mixture, with constant stirring, over a period of 1 minute. The mixture was allowed to stand for 12 hours at 4° C. to complete the polymerization. The resulting free flowing beads comprising Amberlite coated with polyaziridine carrying the immobilized lipase were washed with 5 volumes of 25mM ammonium acetate buffer at pH 6.5. One hundred sixty milliliters of immobilized lipase MY catalyst were recovered.

A series of batch reactions were performed, using this immobilized catalyst. Each batch consisted of 2 moles of R,S-methyl 2-(4-hydroxyphenoxy) propionate (HPPA-Me), 14 moles of toluene, 214 moles of deionized (DI) water, 2 moles of ammonium acetate, and 0.017 moles of sodium dithionite. The pH was adjusted to 6.5 using phosphoric acid. The reaction mixture was stirred for 12 hours to ensure complete solubilization of the HPPA-Me before addition of the immobilized lipase MY.

The immobilized lipase MY was added to the substrate and stirring was continued until the hydrolysis had reached at least 0.8 moles of HPPA acid produced. Samples were taken periodically from the aqueous phase and analyzed as in Example 3. When the conversion of HPPA-Me to HPP reached 40% (800 mMoles HPPA produced) the enzyme beads were removed by filtration and introduced into a new batch of substrate.

The analytical results at the termination of the reaction are given below for eight separate batches run successively using the same immobilized Lipase MY.

TABLE 7

| Batch # | Hydrolysis Time (h) | Total (M) Hydrolysis | % R-HPPA | % S-HPPA |
| --- | --- | --- | --- | --- |
| 1 | 120 | 1 | 82 | 18 |
| 2 | 130 | 1 | 90 | 10 |
| 3 | 140 | 1 | 91 | 9 |
| 4 | 90 | 0.88 | 98 | 2 |
| 5 | 95 | 0.80 | 98 | 2 |
| 6 | 140 | 0.8 | 99 | 2 |
| 7 | 100 | 0.8 | 100 | 0 |
| 8 | 100 | 0.8 | 100 | 0 |

As evident from above, the stereoselectivity of the immobilized Lipase MY increased steadily with usage over the eight batches while the activity of the immobilized lipase MY (% hydrolysis) decreased somewhat. Thus, in the first batch hydrolysis of HPPA-Me to HPPA resulted in the production of 82% R-HPPA and 18% S-HPPA, whereas in both the seventh and eighth batch hydrolysis, the conversion was 100% R-HPPA and 0% S-HPPA. While the activity slightly decreased, this is not a significant disadvantage. The important factor is the increased stereospecificity since an industrial process normally requires greater than 95% ee.

EXAMPLE 10

This examples describes the isoelectric focusing of *Candida rugosa* lipase to determine the compositional profiles.

Samples of commercially available *C. rugosa* lipase from Meito Sangyo, Biocatalyst Ltd, and Amano were examined by isoelectric focusing (IEF) to determine compositional profiles. A protein separation based on net charge was carried out using IEF on a Phast system (Pharmacia LKB) using pre-made IEF gels, pI's 3-9. Enzyme preparations were dissolved in H$_2$O and dialyzed 3 hours prior to IEF. Protein 0.1ug-2.0ug/lane was applied to the gel and run for 590 volt-hr at 15° C. The gels were fixed in 10% trichloroacetic acid and then the protein was stained with silver using a Pharmacia development chamber. The pI's of enzymes were determined by comparison with standards having known pI's.

Figure 2:
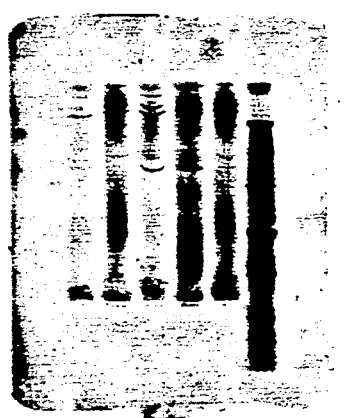

Lipase MY (Meito Sangyo) and Lipase AY (Amano) exhibited very similar profiles (FIG. 2). Each had 4 major protein bands, one with a pI of 5.5, two with pI's near 4.0 and one with a pI near 3.5. Lipase OF (Meito Sangyo) and the *Candida rugosa* lipase (Biocatalyst) had a different profile with 4-5 protein bands with pI's near 4.0. These preparations lacked the enzyme band at a pI of approximately 5.5.

EXAMPLE 11

This example describes the fractionation of Lipase MY from *Candida rugosa* (SP-Trisacryl Chromatography) into two isozyme fractions.

One gram of Lipase MY (Meito Sangyo) was dissolved in 60ml H$_2$O and dialyzed against 2 liters of 0.025M NaH$_2$PO$_4$, pH 3.3 for 16 hours. The insoluble material was removed by centrifugation and the pH was readjusted to 3.3. A 2.5cm×20cm column of SP-Trisacryl (IBF Biotechnics) ion exchanger was prepared and equilibrated with 0.025M NaH$_2$PO$_4$, pH 3.3 (starting buffer). The soluble lipase was applied to the column and unbound material was eluted from the resin with the starting buffer. A separation of the lipase fraction (isozymes) was accomplished with a stepwise pH gradient using a 0.007M citrate-0.015M sodium phosphate buffer. The elution was carried out using the above citrate-phosphate buffer at pH 4.75 to elute the enzyme activity, CSC-2, with continued washing until the A$_{280}$ returned to baseline. The lipase fraction, CSC-1, was then eluted with 150ml of citrate-phosphate buffer pH 6.80. The protein elution profile is shown in FIG. 3. All protein containing fractions were run on IEF (FIG. 4). CSC-1 has a pI of approximately 5.5 wherein CSC-2 had a pI of approximately 4.4.

EXAMPLE 12

This example describes the preparation of stereospecific lipase from Candida rugosa using SP-Sephadex chromatography.

Lipase MY (Meito Sangyo) 1.3 gm in 60 ml of deionized water was dialyzed against 2 liters of 7mM citrate - 15mM Na$_2$HPO$_4$ pH 3.3. The pH of the crude enzyme solution was adjusted to pH 3.3 prior to chromatography. The protein was loaded on a 2.5×20 cm SP - Sephadex column equilibrated in the above citrate - Na$_2$HPO$_4$ buffer at 60 ml/hr at 25° C. The column was washed with 120 ml of the same buffer. A stepwise elution was done with buffers of increasing pH. First, the column was eluted with 100 ml of 7mM citrate 15mM Na$_2$HPO$_4$ pH 4.7 to provide lipase CSC-2 (FIG. 5). Then, the column was eluted with 100 ml of 7 mM citrate - 15mM Na$_2$HPO$_4$ pH 6.8. This buffer eluted a fraction containing the enzyme fraction designated CSC-1.

Based on isoelectric focusing analysis on an IEF 3-9 gel, each of these column fractions contained a single major protein band. The band eluted with pH 4.7 buffer has a pI of 4.4 and is designated CSC-2. The band eluted at pH 6.8 has a pI of 5.2 and is designated CSC-1.

EXAMPLE 13

Amino acid composition and sequence analysis of the isozymes CSC-1 and CSC-2 as obtained from the lipase of *Candida rugosa*.

The purification procedure for CSC-1 and CSC-2 entails an initial solubilization of the Lipase MY at 50 g/Liter in 25 mM dibasic sodium phosphate (final pH of 6.5). After 2-3 hours of stirring at 4° C., the sample was centrifuged (10,000 rpm, 10 minutes) and the pellet discarded. The pH of the supernatant was lowered to 3-3.2 with phosphoric acid, and the supernatant was dialyzed in a hollow fiber device or desalted on a Trisacryl GF-05 column equilibrated in 25 mM sodium phosphate monobasic, pH 3.2. The sample was then loaded onto an SP-Trisacryl column equilibrated at pH 3.2. The column was then washed (25 mM, pH 3.2) and eluted sequentially with pH 4.8 and pH 6.8 citrate/sodium phosphate buffer (McIlvaine buffers, approximately 25 mM). All buffers contained 0.02% sodium azide. The above buffer systems could be replaced with 25 mM sodium acetate, with pH adjustment using acetic acid. It was also possible to perform a buffer and pH exchange on a Trisacryl GF05 column. This column could also be run in distilled water. The predominant bands of the enzymes were found to be localized on SDS-PAGE Phast gels at 55,000–60,000 MW. This band was rather diffuse, and was better characterized using isoelectric focusing (IEF). IEF gels run on the Phast system (pH range 3-9) revealed that the enzymes in the pH 4.8 (first) elution peak (CSC-2) had a pI of approximately 4.4, while those of CSC-1 had a more basic pI (approximately 5.2). These bands were visualized as being at the top (acidic end) of the gel (CSC-2) or near the middle (CSC-1). IEF gels were run on a standard Phast system protocol using a maximum of 2000 volts, 3.5 watts, and a total of 500 volt-hours.

The samples of CSC-1 and CSC-2 were further purified by hollow fiber concentration (CD Laboratories) and/or by a second chromatography on SP-Trisacryl in the case of CSC-2. CSC-1 prepared in this fashion consisted of one major band on IEF gels. CSC-2 contained as many as 4 or more bands, as evidenced by all the closely spaced acidic bands in Lipase MY. The sample of CSC-2 used contained one predominant band. The gel photo (FIG. 6) represents a pH 3-9 IEF Phast gel which was fixed in 20% trichloroacetic acid and silver stained. All samples were diluted in distilled water and loaded onto the gel at 1 microliter per lane. Lanes 1 and 8 were IEF pI standards. These protein standards and their isoelectric points were amyloglucosidase (3.5), methyl red dye (3.75), soybean trypsin inhibitor (4.55), beta lactoglobulin A (5.2), bovine carbonic anhydrase B (5.85), human carbonic anhydrase B (6.55), horse myoglobin (6.85 and 7.35), lentil lectin (8.15, 8.45, and 8.65) and trypsinogen (9.3). Lanes 2 and 3 were samples of Lipase MY (no desalting/purification). Lanes 4 and 5 were of CSC-1, and lanes 6 and 7 were of CSC-2. Since the extinction coefficients of the proteins in the samples were not known, and the absorbance at 280 nm was artificially high due to interfering chromophores, the protein content was estimated by adding 100 ul of the protein solutions to 3 ml of Pierce reagent, and the OD at 595 nm was determined after 10 minutes (spectrophotometer blanked with reagent). In this fashion, 50 mg of lipase MY in 1 ml gave an OD 595 of 0.4 ("400 ug/ml, or "1.8% protein). 1.2 mg of CSC-2 in 1 ml water gave an OD 595 of 0.34 ("340 ug/ml, or "28% protein).

The amino acid composition of CSC-1 and CSC-2 are shown in Table 8.

TABLE 8

| Amino Acid Analysis of CSC-1 and CSC-2 | | |
|---|---|---|
| Amino Acid | % Composition CSC-1 | % Composition CSC-2 |
| Alanine | 9.57 | 8.05 |
| Arginine | 3.62 | 3.5 |
| Aspartic acid/Asparagine | 11.29 | 12.8 |
| Cystine/2 | N.D. | N.D |
| Glutamic acid/Glutamine | 10.76 | 10.6 |
| Glycine | 9.7 | 10.3 |
| Histidine | 1.78 | 1.39 |
| Isoleucine | 4.6 | 4.46 |
| Leucine | 7.9 | 8.3 |
| Lysine | 4.5 | 4.38 |
| Methionine | 1.58 | 1.99 |
| Phenylalanine | 4.3 | 5.0 |
| Proline | 3.0 | 6.59 |
| Serine | 10.9 | 7.9 |
| Threonine | 7.0 | 6.2 |
| Tryptophan | N.D. | N.D. |
| Tyrosine | 3.49 | 3.38 |
| Valine | 5.79 | 4.9 |

*20-hour 6N—HCl/0.05% mercaptoethanol hydrolysis @ 115° C.; one crystal of phenol was added before acid hydrolysis. Serine was increased by 10% and threonine was increased by 5% to compensate for destruction by acid. N.D. not determined.

A sample of CSC-1 was further purified by a C4 reversed phase column and a solvent system of water trifluoroacetic acid 0.07%, acetonitrile trifluoroacetic acid 0.7%. In the system the elution of proteins was obtained by gradient from 20–50% acetonitrile. CSC-2 was similarly resolved by a gradient of 45–75% acetonitrile in the same conditions as those given for CSC-1. CSC-1 and CSC-2 were then separated by electrophoresis, transferred to a PVDF filter (Millipore) and the band migrating at 60,000 daltons was sequenced. Position 10 in CSC-1 could not be assigned with certainty although it may be a tryptophan, which is difficult to identify under the sequencing conditions, possibly due to incomplete carboxymethylation.

The compositions of the novel isozymes, CSC-1 and CSC-2, are illustrated by their N-terminal amino acid sequences as follows:

CSC-1

```
1                 5                    10
Ala—Pro—Thr—Ala—Lys—Leu—Ala—Asn—Gly—(?)
11                15                   20
Thr—Ile—Thr—Gly—Leu—Asn—Ala—Ile—Ile—Asn
21                25                   30
Glu—Ala—Phe—Leu—Gly—Ile—Pro—Phe—Ala—Glu—
31                35
Pro—Pro—Val—Gly—Asn—
```

CSC-2

```
1                 5                    10
Ala—Pro—Thr—Ala—Thr—Leu—Ala—Asn—Gly—Asp—
11                15                   20
Thr—Ile—Thr—Gly—Leu—Asn—Ala—Ile—Ile—Asn—
21                25                   30
Glu—Ala—Phe—Leu—Gly—Ile—X—X—Ala—Glu
31                35              39
Pro—Pro—X—X—Asn—Leu—Phe—Ile—Leu
```

A large sequence homology was seen in CSC-1 and CSC-2 since these enzymes differ only at position 5 and 10 insofar as their sequence is currently known.

It is also noted that there is a large sequence homology of CSC-1 and the acetyl cholinesterase (AcEs) of *Torpedo californica* as shown hereinafter:

```
CSC-1
AcEs
                                              4
                                  Ala—Pro—Thr—Ala
     Asp—His—Ser—Glu—Leu—Leu—Val—Asn—Thr—Lys—
     1                                       10

CSC-1
AcEs
```

-continued
```
         5                  10               14
Lys—Leu—Ala—Asn—Gly—(?)-Thr—Ile—Thr—Gly—
Ser—Gly—Lys—Val—Met—Gly—Thr—Arg—Val—Pro—
11                                           20

CSC-1
AcEs
        15                 20              24
Leu—Asn—Ala—Ile—Ile—Asn—Glu—Ala—Phe—Leu—
Val—Leu—Ser—Ser—His—Ile—Ser—Ala—Phe—Leu—
21                                          30

CSC-1
AcEs
       25                  30              34
Gly—Ile—Pro—Phe—Ala—Glu—Pro—Pro—Val—Gly—
Gly—Ile—Pro—Phe—Ala—Glu—Pro—Pro—Val—Gly—
31                                          40

CSC-2
AcEs
35
Asn—
Asn—
41
```

However, acetylcholinesterase of *T. californica* did not stereoselectively hydrolyze HPPA-Me to R-HPPA in the following test. Two hundred mls of $KH_2PO_4$ (pH 6.5) was combined with 400 mg HPPA-Me and 500 units of *T. californica* acetylcholine esterase. The reaction mixture was shaken for 24 hours and then sampled and analyzed as in Example 3. Very little hydrolyzing activity was observed.

EXAMPLE 14

Large scale separation of Lipase MY isozymes using SP-Trisacryl.

A 10×25cm SP-Trisacryl LS column was equilibrated with 25mM $NaH_2PO_4$ (pH 3.0) (Buffer A). Crude Lipase MY (Meito Sangyo), 150gm, was dissolved in 3.0 liters of 25mM $NaH_2PO_4$ (pH 6.5) for 2 hours. The suspension was centrifuged at 10,000×g for 20 minutes. The soluble fraction was adjusted to pH 3.0 with 5N $H_3PO_4$. The enzyme solution was filtered and dialyzed for 3 hours against 100 volumes of deionized water. The enzyme solution was loaded on the ion exchange column at 1.25 L/hr. Unbound material was washed through the column with buffer A. A two-step pH elution was performed, first with 5 liters of 7mM citric acid-15mM $Na_2HPO_4$ (pH 4.80), followed by 5 liters of 7mM citric acid - 15mM $Na_2 HPO_4$ pH 6.80. The resulting chromatogram is shown in FIG. 7. The protein peak eluted by the (pH 6.80) buffer was pooled and concentrated by ultrafiltration on a hollow fiber device (Amicon). A total of 1.35gm of lipase CSC-1 was recovered from this column. By IEF, this protein was identical with lipase CSC-1 produced in Example 11.

EXAMPLE 15

Hydrolysis of HPPA-methyl ester with lipase CSC-1.

R,S HPPA-methyl ester (25mM) in 25 ml of 50mM $Na_2HPO_4$ pH 6.5 was hydrolyzed at 25° C. with 50ug of lipase CSC-1 enzyme (from Example 11). After 1 hour of reaction, a sample was removed and analyzed by high pressure liquid chromatography, wherein the R and S acids were separated and their respective concentrations determined. A Resolvosil-BSA-7 (Macherey-Nagel) analytical column (150×4mm) was used with 10mM $KH_2PO_4$ pH 5.0, 5% n-propanol as the mobile phase at 2.0ml/min. At that time the reaction contained 2.9 mM R-acid and no detectable S-acid. The reaction was allowed to proceed to 46% conversion of the racemic ester, at which time the ratio of the acids formed was 97% R-acid and 3% S-acid.

EXAMPLE 16

Hydrolysis of HPPA-ethyl ester with free lipase CSC-1.

25ml of R,S HPPA-ethyl ester (20mM) in 50mM $Na_2HPO_4$ pH 6.5 was hydrolyzed at 25° C. with 1 mg of the enzyme, CSC-1. After 1 hour of reaction, a sample was removed and analyzed by high pressure liquid chromatography, to determine the concentration of the R and S acids. A Resolvosil-BSA-7 (Macherey-Nagel) analytical column (150×4mm) was used with 10mM $KH_2PO_4$ (pH 5.5), 5% n-propanol as the mobile phase at 2.0ml/min. At 1 hour, a 30% hydrolysis of the racemic ester had occurred and the enantiomeric purity of the acid produced was 98% R-acid and 2% S-acid.

EXAMPLE 17

Comparison of CSC-1 and CSC-2 in the hydrolysis of HPPA-methyl ester.

Twenty five mls of 25 mM HPPA-Me/100mM $KH_2PO_4$ (pH 6.5) buffer were placed into each of two 100ml Erlenmeyer flasks. CSC-1 (50ul fraction as eluted from the SP-Trisacryl column, Example 11) was placed in a flask and CSC-2 (50ul, fraction from SP-Trisacryl column, Example 11) was placed in the other flask. The reactions were sampled as noted below and analyzed as in Example 3 with the following results.

TABLE 9

| Time (Hr) | CSC-1 % Conversion | % R-HPPA | CSC-2 % Conversion | % R-HPPA |
|---|---|---|---|---|
| 1 | 4 | 100 | 5 | 97 |
| 2 | 11 | 100 | 7 | 96 |
| 3 | 17 | 100 | 8 | 97 |
| 5 | 25 | 99 | 13 | 96 |
| 22 | 52 | 97 | 40 | 93 |
| 30 | — | — | 49 | 91 |

As indicated, the rate of conversion of racemic HPPA methyl ester was substantially higher for CSC-1. The enantiomeric purity of the product obtained with CSC-1 was also superior compared to that obtained with CSC-2 although both gave useful results.

EXAMPLE 18

This example compares the results obtained by hydrolyzing ketoprofen esters using CSC-2 and crude lipase MY.

To a solution of 9ml of 100mM ammonium phosphate (pH 5.5) in 50 ml Erlenmeyer flask a weighed amount of ester (either directly or dissolved in 200 ul DMF) was added. A solution of the weighed amount of enzyme in 1 ml of the same buffer was added. The mixture was agitated in a rotary shaker at 250 RPM at 35° C. typically for 22 hours. The reaction mixture was acidified with 8 drops 6(N) HCl to pH 1.5–2.0, extracted with $CHCl_3$ (2×10 ml). The $CHCl_3$ solution was analyzed by HPLC to determine the percent of acid produced in the hydrolysis.

The $CHCl_3$ extract (5 ml) of the hydrolysis reaction was dried over anhydrous $Na_2SO_4$ and filtered. The filtrate was cooled to 0° C. in stoppered vials and 100 ul of N-methylmorpholine, followed by 100 ul of isobutyl chloroformate were added. After gently shaking at 0°

C. for 10 minutes, 100 ul of D-(+)-1-phenylethylamine was added and gently shaking at 0° C. was continued for 5 minutes. The reaction mixture was then shaken at room temperature for 5 minutes. The reaction mixture was washed with water (5 ml), 1(N) HCl (5 ml) and again with water (5 ml). The diastereomeric amides produced were then analyzed by HPLC on a column as specifically noted to determine the ee (%S-%R) of the acid produced by enzymatic hydrolysis of the esters.

Ketoprofen esters (50 mg) were hydrolyzed as above. HPLC analysis for the amount of acid produced for the ketoprofen monoglyceride and ketoprofen ethylene glycol ester hydrolysis were performed on Partisil 5 ODS-3 RAC column (9.4 mm×100 mm, Whatman) using $CH_3OH$: 10mM $(NH_4)H_2PO_4$(60:40) at 4 ml/min and monitoring at 254 nm. HPLC analysis of the acid produced in the hydrolysis of the other esters were done on ODS-3 RAC column using $CH_3OH$: 10 mM $(NH_4)H_2PO_4$ (80:20) at 2ml/min and monitoring at 254 nm. The enantiomeric excess of the ketoprofen produced for each hydrolysis was determined by analysis of the amides by HPLC on ODS-3 RAC column using $CH_3OH$:10 mM $(NH_4)H_2PO_4$ (60:40) at 4 ml/min and monitoring at 254 nm. The results are tabulated below:

TABLE 10

Results of Hydrolysis of Various Esters of Ketoprofen with CSC-2 and Comparison of the Results with Crude Lipase MY

| Ester | Enzyme | Reaction in | Rate umole/h/mg | ee of S-acid (%) |
|---|---|---|---|---|
| methyl | Lipase MY | Buffer | 0.002 | 36 |
|  | CSC-2 | Buffer | 0.222 | 96 |
| n-butyl | Lipase MY | Buffer | 0.005 | 88 |
|  | CSC-2 | Buffer | 0.519 | >99 |
|  | CSC-2 | Two phase* | 0.314 | >99 |
| n-octyl | Lipase MY | Buffer | 0.004 | 94 |
|  | CSC-2 | Buffer | 0.192 | ND |
|  | CSC-2 | Two phase* | 0.069 | ND |
| 2-chloroethyl | Lipase MY | Buffer | 0.014 | 32 |
|  | CSC-2 | Buffer | 1.405 | 98 |
|  | CSC-2 | Two phase* | 2.735 | 98 |
| 2,2,2-trifluoroethyl | Lipase MY | Buffer | 0.023 | 15 |
|  | CSC-2 | Buffer | 2.931 | 78 |
|  | CSC-2 | Two phase* | 1.855 | 81 |
| monoglyceryl | Lipase MY | Buffer | 0.034 | 77 |
|  | CSC-2 | Buffer | 2.079 | 98 |
|  | CSC-2 | Two phase* | 3.815 | ND |

*Isooctane — 100 mM $(NH_4)H_2PO_4$ (pH 5.5) (1:1) two phase system.
ND = Not Determined As will be evident, much better ee values and rates of hydrolysis were obtained using CSC-2 when compared with Lipase MY in the hydrolysis of esters of ketoprofen.

This example also shows useful results (for example, high rate and ee) using a two-phase system which includes isooctane.

EXAMPLE 19

This example compares the results obtained in the hydrolysis of ketoprofen monoglyceride using crude Lipase MY, CSC-1 and CSC-2.

To a solution of 9 ml of 100 mM ammonium phosphate buffer (pH 5.5) 50 mg of ketoprofen monoglyceride either as such or in 200ul DMF was added followed by a solution of enzymes in 1 ml of the same buffer. After shaking at 250 rpm at 35° C. for 22 hours, the reaction mixtures were acidified and extracted with chloroform (2×10 ml) and analyzed by HPLC to determine the amount of acid produced and analyzed as in Example 18. The results are given below:

TABLE 11

Results of Hydrolysis of Ketoprofen monoglyceride

| DMF | Enzyme | Percent of Acid | Percent of Acid from Hydrol | Rate | EE of S-acid (%) | Calc. EE of S-acid (%)* |
|---|---|---|---|---|---|---|
| 200 ul | No Enzyme | 0.3 |  |  |  |  |
| 0 ul | No enzyme | 0.4 |  |  |  |  |
| 200 ul | Lipase MY (50 mg) | 28.3 | 28.0 | 0.039 | 75.2 | 76.0 |
| 0 ul | Lipase MY (50 mg) | 27.2 | 26.8 | 0.037 | 68.0 | 69.0 |
| 200 ul | CSC-2 (1 mg) | 21.3 | 21.0 | 1.455 | 95.4 | 96.6 |
| 0 ul | CSC-2 (1 mg) | 27.7 | 27.3 | 1.891 | 96.4 | 97.8 |
| 200 ul | CSC-1 (1 mg) | 3.6 | 3.3 | 0.229 | 74.6 | 81.0 |
| 0 ul | CSC-1 (1 mg) | 4.5 | 4.1 | 0.284 | 84.6 | 92.6 |

*Calculated by subtracting the R- and S-acid present in the starting material as impurity These results indicate that CSC-2 is preferred for use with ketoprofen monoglyceride because of its substantially higher hydrolysis rate and better enantiomeric excess (ee).

EXAMPLE 20

Effect of dimethylformamide (DMF) on hydrolysis.

Hydrolysis of ketoprofen-monoglyceride (50mg) was carried out in various DMF-100mM $(NH_4)H_2PO_4$ buffer (pH 5.5) mixtures. In each flask a solution of ketoprofen monoglyceride (50mg) in DMF (200ul) was added. DMF was added followed by 100mM $(NH_4)H_2PO_4$ buffer. A solution of 1mg purified CSC-2 in 0.5ml buffer was added. After 22 hours, 2%, 5%, and 10% DMF samples were acidified, extracted with $CHCl_3$ (2×10ml) and analyzed. The other samples were analyzed directly as in Example 18. The acid produced decreases with increasing amount of DMF.

| % DMF | % acid |
|---|---|
| 2 | 23 |
| 5 | 18 |
| 10 | 11 |
| 20 | 3 |
| 30 | 0.7 |
| 40 | 0.3 |
| 50 | 0.4 |

EXAMPLE 21

Large scale hydrolysis of ketoprofen monoglyceride.

To a solution of 100 mg CSC-2 in 500 ml of 100 mM ammonium phosphate buffer (pH 5.5) in a 2.8 L Fernbach flask, a solution of 10 g of ketoprofen monoglyceride in 10 ml DMF was added. After shaking in a rotary shaker at 300 rpm at 35° C. for 166 hours, the reaction mixture was adjusted to pH 10 with 1 M NaOH and extracted with ethyl acetate (3×500 ml) to remove the neutral fraction (containing the ketoprofen ester). The aqueous layer (containing ketoprofen acid) was acidified to pH 1.5 with 6 N HCl and extracted with ethyl acetate (3×500 ml). Removal of solvents from the ester and acid afforded 6.55 g (65.5%) of crude ester and 2.32 g (30%) of crude acid respectively. The crude acid was crystallized from aqueous ethanol to provide 1.69 g (21.8%) of ketoprofen as white powder. The acid was found by HPLC of the amides as in Example 18, to have 91.2% enantiomeric excess for the S-acid.

EXAMPLE 22

The effect of DMF and surfactants on the hydrolysis of ketoprofen monoglyceride (KPG) to ketoprofen (KP) using CSC-2 is shown in this example. The surfactants used were Tween 80 and Span 85.

Small amounts of DMF were added to the reaction mixture to increase the solubility of KPG. In all cases 100mM ammonium phosphate buffer (pH 5.5) was used and 2% (v/v) detergents were added and the total volume was 10ml. The KPG was either added directly or dissolved in 200ul DMF. In all cases the enzyme to substrate ratio was 1:50. The results obtained by analysis as in Example 18 are given below.

TABLE 12

Effect of DMF on the hydrolysis of KPG in presence of detergents

| KPG (mg) | DMF (ul) | Tween-80 in buffer | | | Span-85 in buffer | | |
|---|---|---|---|---|---|---|---|
| | | Rate | Rel. Rate | % ee | Rate | Rel. Rate | % ee |
| 50 | 200 | 1.63 | 100[1] | 96 | 1.37 | 100[2] | 93 |
| 100 | 200 | 0.64 | 40 | 92 | 2.39 | 175 | 96 |
| 200 | 200 | 0.28 | 17 | 86 | 1.47 | 107 | 95 |
| 50 | 0 | 2.10 | 129 | 97 | 3.69 | 269 | 97 |
| 100 | 0 | 1.62 | 99 | 96 | 2.97 | 216 | 97 |
| 200 | 0 | 1.04 | 64 | 93 | 1.70 | 124 | 95 |

[1] = Assigned 100 as standard for all reaction in Tween-80
[2] = Assigned 100 as standard for all reaction in Span-85

The results obtained indicate the detrimental effect of DMF on rate and ee. The use of surfactants give good rate and ee.

EXAMPLE 23

Hydrolysis of ketoprofen monoglyceride in aqueous-organic two phase system.

Ketoprofen monoglyceride (10.9 mg) in DMF (50 μl) was added to various organic solvents (2 ml each) and a solution of CSC-2 (0.4 mg) in 100 mM ammonium phosphate buffer (pH 5.5, 2 ml) was added to each. The buffer reaction (entry #2 in the table) contained enzyme in buffer (2 ml) and the buffer only (entry #1 in the table) reaction contained no enzyme.

After shaking at 150 rpm, the reaction mixtures were analyzed by standard methods as in Example 18. The results are given in Table 13.

TABLE 13

Hydrolysis of ketoprofen monoglyceride by CSC-2 in aqueous-organic two phase systems

| No | Solvent | Relative Rate | EE of S-acid (%) |
|---|---|---|---|
| 1 | Buffer only (No enzyme)* | | |
| 2 | Buffer | 100 | 96 |
| 3 | Hexane | 80 | 93 |
| 4 | Isooctane | 214 | 96 |
| 5 | Cyclohexane | 185 | 95 |
| 6 | Cyclohexene | 146 | 89 |

TABLE 13-continued

Hydrolysis of ketoprofen monoglyceride by CSC-2 in aqueous-organic two phase systems

| No | Solvent | Relative Rate | EE of S-acid (%) |
|---|---|---|---|
| 7 | Cyclooctene | 387 | 95 |
| 8 | Toluene | 15 | 58 |
| 9 | Xylenes | 44 | 81 |
| 10 | Ethylbenzene | 18 | 48 |
| 11 | Cumene | 91 | 86 |
| 12 | 1,2,3,4-Tetrahydronapthalene | 136 | 85 |
| 13 | Carbon tetrachloride | 48 | 95 |
| 14 | Chloroform S | 0 | |
| 15 | Dichloromethane S | 0 | |
| 16 | 1,1,1-Trichloroethane | 25 | 75 |
| 17 | Ethylene dichloride S | 0 | |
| 18 | 1,1,2-Trichloroethane S | 0 | |
| 19 | Tetrachloroethylene | 3 | 27 |
| 20 | 1,1,2-Trichlorotrifluoroethane | 123 | 99 |
| 21 | Ethyl ether S | 0 | |
| 22 | Isopropyl ether | 53 | 69 |
| 23 | n-Butyl ether | 59 | 69 |
| 24 | Cyclohexanone S | 0 | |
| 25 | 3-Pentanone S | 0 | |
| 26 | n-Butanol S | 0 | |
| 27 | n-Hexanol S | 0 | |
| 28 | n-Octanol S | 0 | |
| 29 | Benzyl alcohol S | 0 | |
| 30 | Ethyl acetate S | 0 | |

*All values in the table were corrected for this control
S 16 hour reactions, all others 26 hours The following results show that certain low polarity solvents can be used to improve the rate of hydrolysis with minor effects on the enantiomeric excess.

EXAMPLE 24

The immobilization of CSC-2 and its use in the hydrolysis of ketoprofen monoglyceride.

To 10 ml 100 mM ammonium phosphate (pH 5.5) a solution of 50 mg ketoprofen monoglyceride in 200 ul DMF was added followed by CSC-2 (immobilized by different methods and containing the equivalent of 2 mg of CSC-2). After shaking at 250 rpm at 35° C., the reaction mixtures were acidified, extracted with chloroform and analyzed by HPLC as in Example 18. The results are given in Table 4. The methods of immobilization are as follows:

(1) 269-I

Lipase CSC-2 2mg was mixed with 0.3g of Amberlite DP-1 and 200 mg of XAMA-7 in 10ml of cyclooctene. The mixture was shaken at room temperature for 4 hours before the cyclooctene was evaporated. The immobilized enzyme was washed with DI water and stored at 4° C.

(2) 269-II

Same as 269-I, except 50mg of stearic acid was added.

(3) 269-III

Same as 269-I, except 50mg of hexadecylamine was added.

(4) 269-2A to 2G

Same as 269-II. Amberlite DP-1 was pH adjusted as follows:
2A pH 3.5
2B pH 4.5
2C pH 5.5
2D pH 6.5
2E pH 7.5

2F pH 8.5
2G pH 9.5

(5) 269-5A

Lipase CSC-2, 2mg, dissolved in 1ml of phosphate buffer (0.01M, pH 6.5) was shaken with the sodium periodate (5%) activated cellulose beads (0.5g) at room temperature. The immobilized enzyme was washed with deionized water and stored at 4° C.

(6) 269-5B

Lipase CSC-2, 2mg, dissolved in 1ml of phosphate buffer (0.01 M, pH 6.9) was shaken with 0.58g of Affi-Prep 10 at room temperature for 24 hrs. The immobilized enzyme was washed and stored at 4° C.

(7) 269-7F

Amberlite DP-1 resin was equilibrated at pH 3.5, washed with acetone and dehydrated at 100° C. Lipase CSC-2, 2mg, in 1 ml of phosphate buffer (0.01M, pH5.0) was mixed with 0.3g of the dehydrated resin and the mixture was lyophilized. The lyophilized enzyme was shaken in 5ml of cyclooctene containing stearic acid (50mg) and XAMA-7 (50mg) at room temperature and cyclooctene was allowed to evaporate overnight. The immobilized enzyme was washed and stored at 4° C. Cellulose beads were used to prepare 269-7G by the same procedure, Dowex 50w ×4 was for 269-7E and Amberlite A15 was for 269-7D.

(8) 269-8A

Same as 269-7F but with XAMA-2.

269-8B

Same as 269-7F.

(9) 269-9A

Lipase CSC-2, 2mg was shaken with 0.5 g of Na$_2$O$_4$ activated cellulose beads in pH 5.0 buffer for 20 hours. The enzyme was collected, washed and stored at 4° C.

(10) 269-9B

Same as 269-9A but at pH 7.0.

(11) 269-10

Lipase CSC-2, 25.1 mg was mixed with 0.2g of CM-cellulose in 5 ml of cyclooctene containing 1.0 ml of 10% stearic acid. The mixture was shaken for one hour before the addition of 2.0 ml of 10% XAMA-7 in the same solvent. The mixture was shaken at room temperature overnight and cyclooctene was evaporated. The immobilized enzyme was collected, washed and stored at 4° C.

(12) 269-11A and 269-11D

Lipase CSC-2, 10mg and glucose 150mg in 5ml of deionized water were mixed with 1.25g of Amberlite DP-1 (pH 3.5) and the mixture was lyophilized. The lyophilized enzyme was shaken in 20ml of cyclooctene (269-11A) or 1,1,2trichlorotrifluoroethane (269-11D) with 250mg of XAMA-2 and 500mg of stearic acid. This procedure was used to prepare 269-11B, 269-11C, 269-11E and 269-11F.

(13) 269-12A

Same as 269-9B but with 0.1% EDTA. 269-12B Same as 269-12A but at pH 8.5.

(14) 269-13

Same as 269-8A, but 110 mg of starch was added.

(15) 269-14A

Lipase CSC-2, 10mg, in 5ml of deionized water was mixed with 1g of dehydrated cellulose beads and the mixture was lyophilized. The lyophilized enzyme was immobilized in 20ml of cyclooctene with 400mg of stearic acid and 200mg of XAMA-2. CM-cellulose beads were used to prepare 269-14B. (16) 279-SD1.

To 1 g of silica (Spherosil, 400 LS, IBF) a solution of 10 mg of lipase CSC-2 in 4 ml of 100 mM ammonium phosphate buffer (pH 5.5) was added and the mixture was gently shaken for 22 hours. The solids were filtered off, washed with the same buffer (5×10 ml). The solution was found to possess no activity, all the activity was retained in the solid.

TABLE 14

| Code | Activity (%) of Free CSC-2 | % ee of S-acid |
|---|---|---|
| Immobilization with DP-1 | | |
| 269-I | 1 | ND |
| 269-II | 23 | 70 |
| 269-II | 5 | ND |
| 269-2A to -2G | 1-5 | ND |
| 269-7F | 51 | 80 |
| 269-8A | 9 | ND |
| 269-8B | 38 | 70 |
| 269-11A | 41 | 81 |
| 269-11D | 22 | 81 |
| 269-13 | 4 | ND |
| Immobilization with cellulose | | |
| 269-7G | 59 | 87 |
| 269-11B | 31 | 76 |
| 269-11E | 7 | ND |
| 269-14A | 48 | 87 |
| Immobilization with CM-cellulose | | |
| 269-10 | 7 | ND |
| 269-11C | 50 | 82 |
| 269-11F | 40 | 82 |
| 269-14B | 61 | 85 |
| Immobilization with periodate activated cellulose | | |
| 269-5A | 27 | 96 |
| 269-9A | 10 | 92 |
| 269-9B | 17 | 93 |
| 269-12A | 7 | ND |
| 269-12B | 7 | ND |
| Immobilization with other supports | | |
| 269-5B | 11 | 76 |
| 269-7D | 1 | ND |
| 269-7E | 6 | ND |
| 269-SD1 | 107 | 97 |

ND = Not determined

EXAMPLE 25

Immobilization of purified lipase isozyme CSC-1 on Eupergit C and its use in hydrolysis.

Eupergit C resin (Hoechst) 1gm, was washed with 20 volumes of 0.1 M Na$_2$HPO$_4$ pH 6.0. Six ml of the same buffer containing 3.0mg of purified lipase was added to the resin and allowed to react at 4° C. with gentle mixing for 16 hours. This catalyst was then washed with 10 volumes of buffer pH 6 0. The catalyst was added to 100ml of 25mM HPPA-Me in 50mM Na$_2$HPO$_4$ pH 6.5 at 25° C. and gently shaken. The recovery of immobilized enzyme activity relative to soluble enzyme was 39%, based on HPLC assays of ester conversion to R and S acid. At 42% hydrolysis of the R-S ester the acid ratio was 97% R.

EXAMPLE 26

This example describes the effect of organic acids on the immobilization of lipase MY.

Lipase MY (0.45g), dehydrated Amberlite DP-1 (0.9g) and XAMA-7 (pentaerythritol-tris-{beta-N-aziridinyl} propionate), (100mg), were mixed in 10ml of toluene containing one of the following saturated acids: propionic acid (30mg), butyric acid (30mg) valeric acid (30mg), hexanoic acid (30mg), heptanoic acid (30mg) octanoic acid (40mg), nonanoic acid (40mg) decanoic acid (40mg) undecanoic acid (40mg), lauric acid (40mg), tridecanoic acid (40mg), myristic acid (40mg) pentadecanoic acid (50mg), palmitic acid (50mg), heptadecanoic acid (50mg), stearic acid (50mg), docosanoic acid (30mg), eicosanoic acid (50mg) and tetracosanoic acid (50mg). The mixtures were shaken at room temperature and the toluene was then gently evaporated. The immobilized enzyme preparations were hydrated, washed with deionized water and assayed. As shown in FIG. 8, an 18 carbon acid, stearic acid, gave superior immobilization yields.

EXAMPLE 27

The effect of stearic acid on lipase activity.

Lipase MY 0.45g, dehydrated Amberlite DP-1, 0.9g, and XAMA-7, 100mg were mixed in 10ml of toluene containing 4.5, 11.25, 22.5, 45 and 90mg of stearic acid by the procedure in Example 24. The results are shown in FIG. 9.

EXAMPLE 28

Optimization of stearic acid addition for immobilization.

Lipase MY, 3.6g. in 200ml of sodium acetate buffer (1M, pH 3.5) was shaken with 27g of Amberlite DP-1, the pH was adjusted to 4.5 with acetic acid. The mixture was shaken at 4° C. overnight and the beads were collected, washed with deionized water and lyophilized to give 8.1g of dried beads. The beads (1g) were then added to 10ml of toluene containing 100mg of XAMA-7 and 10, 25, or 50mg of stearic acid and gently mixed. The assay results obtained as in Example 24 are shown in FIG. 10.

EXAMPLE 29

Immobilization of CSC-1 with polyaziridine.

Five hundred mg of CSC-1 isozyme was combined with 0.5 grams of 75% hydrolyzed polyvinyl alcohol (3000 MW) and 230 ml of ice cold deionized water and was mixed for 15 minutes. To the mixture was added 100 grams of dry Amberlite DP-1 (Rohm-Haas) ion exchange resin at pH 7.0. The mixture was allowed to stand for 20 minutes at room temperature before the material was lyophilized. Upon completion of the lyophilization, a mixture of 140 ml of toluene and 3.5 grams of stearic acid was added to the beads and allowed to stand one hour. 40 ml of toluene and 7 grams XAMA-7 polyaziridine prepolymer were added to the mixture and a like amount added again one hour later. The mixture was covered and slowly shaken for a period of 4 hours at which time the toluene was slowly evaporated. The immobilized enzyme preparation was washed with two 250 ml aliquots of deionized water.

The activity of purified CSC-1 in a soluble form was determined to be 550 uMoles/hr/mg at 35% conversion of HPPA-Me to HPPA. The immobilized CSC-1 from this experiment was found to have an activity of 920 uMoles/hr/g immobilized beads at 37% conversion or 231 mMoles/hr for the total batch. The washing of the beads were found to have an activity of 32 mMoles/hr for all washings. On this basis, 84% of the enzyme activity was immobilized, 12% was found in the wash material, and 4% of the activity was unaccounted for.

EXAMPLE 30

This example illustrates the effect of polyvinyl alcohol (PVA) on the immobilization of lipase CSC-1 and its activity.

Lipase CSC-1 5mg in 5ml of DI water was lyophilized with Amberlite DP-1 (0.3g) and 0, 10, 20, 30, 40 and 50mg of polyvinyl alcohol (MW 3,000, 75% hydrolyzed or MW 10,000, 88% hydrolyzed). The enzyme was then immobilized with 50mg of stearic acid and 50mg of XAMA-7 in 6ml of toluene. After the toluene was evaporated, the immobilized enzyme was assayed with HPPA-Me and the relative activity of the enzyme was calculated.

| PVA (MW 3,000) (mg) | Relative Activity (%) |
|---|---|
| 0 | 100 |
| 10 | 149 |
| 20 | 145 |
| 30 | 143 |
| 40 | 136 |
| 50 | 153 |
| 0 | 100 |
| 10 | 119 |
| 20 | 123 |
| 30 | 126 |
| 40 | 121 |
| 50 | 97 |

The above results show that PVA addition serves to increase the relative activity of lipase CSC-1.

EXAMPLE 31

Immobilization of crude Lipase MY.

One gram of lipase MY was combined with 25 ml of 25 mM $Na_2HPO_4$ pH 6.5 and mixed well for 20 minutes and then centrifuged. The supernatant was chilled to 10° C. and was added to 13 milliliters of dry Amberlite DP-1 (pH 7.0). This material was then lyophilized. A mixture of 16 ml of toluene and 0.42g stearic acid was added, to the lyophilized material, and shaken for one hour. A mixture of 10 ml of toluene and 2.5g XAMA-7 prepolymer was then added over a period of one hour. The mixture was covered and allowed to shake for four hours after which the toluene was gently evaporated. The beads were washed twice with 100ml aliquots of deionized water. A comparison of the hydrolytic activity on HPPA-Me of Lipase MY and immobilized lipase MY showed the activity of Lipase MY was 4700 uMoles/hr/g at 17% conversion of HPPA-Me to HPPA. Immobilized lipase MY had an activity of 2160 uMoles/hr/batch at 16% conversion. The washings had an estimated activity of 175 uM/hr/batch. Thus, 50% of enzyme activity remained, of the original activity, 46% was immobilized and 4% was in the wash.

EXAMPLE 32

Isolation of R- 2-(4-hydroxyphenoxy) propionic acid.
RS-HPPA-methyl ester (2 moles; 392 gm) was dissolved in 1500ml of toluene. Three liters of 0.58 M ammonium acetate pH 6.5 and 3 g Na$_2$S$_2$O$_4$ was added to the toluene. Immobilized lipase MY (160 ml, as prepared in Example 9), was added to the two-phase substrate mixture above and allowed to react with agitation at 25° C. for 120 hours. At this time, 40.8% of the ester was hydrolyzed. The aqueous phase was separated from the organic layer and adjusted to pH 7.0. This phase was extracted 4 times with 0.25 volumes of methylene chloride to remove the ester. The aqueous phase was adjusted to pH 2.5 and extracted 4 times with 0.25 volumes of ethyl acetate. Solid MgSO$_4$ (anhydrous) was added to the ethyl acetate to remove the water, and the organic layer was filtered. Ethyl acetate was removed under reduced pressure at 50° C. leaving solid R-2-(4-hydroxyphenoxy) propionic acid. The acid contained 95% R-acid an 5% S-acid.

EXAMPLE 33

This example demonstrates the improved lifetime of immobilized CSC-1 catalyst.

Immobilized CSC-1 (19 ml) as prepared in Example 29. was placed into a 1 cm×24 cm chromatography column. This material was then washed with 50 column volumes of deionized water to remove any unbound protein. 25mM HPPA-Me substrate was prepared by combining 34.8g K$_2$HPO$_4$, 4 liters deionized water, and 4g sodium dithionite, adjusting the pH to 6.5 using phosphoric acid and then adding 19.6 grams R,S-HPPA-Me. This solution was passed over the enzyme at 0.75 ml/min (2.4 column volumes/hr). Samples were analyzed daily to determine the enzymatic activity of the catalyst.

As shown in FIG. 11 the column was run for a period of 40 days with no apparent loss of catalyst activity.

EXAMPLE 34

Preparation of lipase from *Candida rugosa* by QA-Trisacryl M chromatography.

As an alternative method of isolating CSC I lipase, 2.1 gm of Lipase MY (Meito Sangyo) was dissolved in 32 ml of DI water and dialyzed against 25 mM Na$_2$HPO$_4$. pH 6.3. Solids were removed by centrifugation. The protein was applied to a QA-Trisacryl M (IBF) column, 2.5×4.0 cm equilibrated in 25 mM histidine - HCl pH 6.0 at 62 ml/hour. The column was washed with the same buffer until absorbance at 280 nm reached baseline. A large unbound A$_{280}$ peak was recovered containing lipase CSC I and 4-5 minor protein components, based on IEF pH 3-9 analysis using a Pharmacia Phast gel system.

Protein bound to the QA-Trisacryl M column was eluted using a 200 ml 0.-0.3 M NaCl gradient in 25 mM histidine-HCl pH 6.0.

A representative fraction of CSC I was assayed for stereoselective hydrolysis of R, S-HPPA-methyl ester as described in Example At 41% conversion, the product was 98% R-acid.

EXAMPLE 35

Hydrolysis of ibuprofen methyl ester.

Ibuprofen methyl ester (200 mg) was subjected to enzymatic hydrolysis as in Example 18 and the amount of acid produced was determined by HPLC on ODS-3 RAC column using CH$_3$OH: 10mM (NH$_4$)H$_2$PO$_4$ (80:20) 2 ml/min and monitoring at 220 nm. The ee of the acid produced was determined by converting to the diasteromeric amide as in Example 18 and analysis by HPLC on a Hibar RT Lichrosorb Si60 column (5 um, 4 mm×25 cm, E. Merck) using CH$_2$Cl$_2$ CH$_3$CN (96:4) as eluant at 2ml/min and monitoring at 254 nm. The results are given in the Table below.

TABLE 15

| Results of Hydrolysis of Ibuprofen Methyl Ester | | | | | |
|---|---|---|---|---|---|
| Flask | DMF | Enzyme | Percent of Acid | Rate uMole/hr/mg | % ee of S-acid |
| 1* | 200 ul | No Enzyme | 0 | | |
| 4 | 200 ul | Lipase MY (50 mg) | 29 | 0.2 | 96 |
| 5 | 0 ul | Lipase MY (50 mg) | 28 | 0.2 | 96 |
| 6 | 200 ul | CSC-2 (1 mg) | 32 | 13.3 | 97 |
| 7 | 0 ul | CSC-2 (1 mg) | 28 | 11.4 | 98 |
| 8 | 200 ul | CSC-1 (1 mg) | 4 | 1.8 | 96 |
| 9 | 0 ul | CSC-1 (1 mg) | 5 | 2.1 | 95 |

*100 mg of ibuprofen methyl ester was used for this control experiment

EXAMPLE 36

Hydrolysis of fenoprofen methyl ester:

The ester was used as such without any DMF. Fenoprofen methyl ester (56 mg or 112 mg) was subjected to the enzymatic hydrolysis according to Example 18 and the amount of acid produced was determined by HPLC on ODS-3 RAC column using CH$_3$OH: 10mM (NH$_4$)H$_2$PO$_4$ (60:40) as eluant at 4 ml/min and monitoring at 254 nm. The ee of the acid produced was determined by converting to the diastereomeric amides as in Example 18 and then analysis by HPLC on Hibar Lichrosorb Si60 (5um) column using CH$_2$Cl$_2$:CH$_3$CN (96:4) at 2 ml/min and monitoring at 254 nm. The results are given in the table below.

| Hydrolysis of the Methyl Ester of Fenoprofen | | | | |
|---|---|---|---|---|
| Ester | Enzyme | Acid (%) | Rate uMole/hr/mg | ee of S-acid (%) |
| 56 mg | No enzyme | 0 | | |
| 56 mg | Lipase MY (50 mg) | 16 | 0.03 | 80 |
| 112 mg | Lipase MY (50 mg) | 17 | 0.07 | 89 |
| 56 mg | CSC-2 (1 mg) | 22 | 2.2 | 96 |
| 112 mg | CSC-2 (1 mg) | 13 | 2.6 | 96 |
| 56 mg | CSC-1 (1 mg) | 20 | 2.0 | 95 |
| 112 mg | CSC-1 (1 mg) | 14 | 2.8 | 96 |

EXAMPLE 37

This example describes the hydrolysis of 2-phenylpropionic acid methyl ester.

The ester was subjected to enzymatic hydrolysis without addition of DMF as carried out in Example 18. The amount of acid produced was determined by HPLC on ODS-3 RAC column using CH$_3$OH: 10 mM (NH$_4$)H$_2$PO$_4$ (60:40) at 4 ml/min and monitoring at 220 nm. The acid produced in the reaction was converted to the diastereomeric amides as in Example 18 and analyzed by HPLC on Hibar Lichrosorb Si60 (5 um) column using CH$_2$Cl$_2$:CH$_3$CN (98:2) at 2 ml/min and monitoring at 254 nm to determine the enantiomeric excess. Results are given in the Table 16 below.

TABLE 16

| Hydrolysis of the methyl ester of 2-phenylpropionic acid | | | | |
|---|---|---|---|---|
| Ester (mg) | Enzyme | Percent Acid | Rate uMole/hr/mg | ee of S-acid (%) |
| 43.7 | Lipase MY (50 mg) | 28 | 0.07 | 88 |
|  |  | 31 | 0.08 | 88 |
| 46.7 | CSC-2 (1 mg) | 18 | 2.4 | 93 |
|  |  | 17 | 2.1 | 93 |

TABLE 16-continued

| Hydrolysis of the methyl ester of 2-phenylpropionic acid | | | | |
|---|---|---|---|---|
| Ester (mg) | Enzyme | Percent Acid | Rate uMole/hr/mg | ee of S-acid (%) |
| 47.4 | CSC-1 | 9 | 1.2 | 91 |
|  | (1 mg) | 9 | 1.2 | 89 |

EXAMPLE 38

This example describes the hydrolysis of Indoprofen monoglyceride. Indoprofen monoglyceride (50 mg) was subjected to hydrolysis as in Example 18 with higher quantities of the enzymes as shown in Table 17. After 68 hours the reaction was extracted according to the procedure shown in Example 18 and the amount of acid produced was determined by HPLC on ODS-3 RAC column using $CH_3OH$-10 mM $(NH_4)H_2PO_4$ (60:40) at 4 ml/min and detection at 254 nm. The enantiomeric excess was determined by HPLC of the diastereomeric amide (prepared as in Example 18) on the same system. The R- and S- isomer of the amide of authentic RS-indoprofen gave peaks of slightly different area, and the enantiomeric excess was calculated by accounting for this difference. In addition, a small amount of the reaction mixture was separated into the acid and ester by extraction with $NaHCO_3$ and the rotations of these were determined and reported below. By analogy with other profens, the acid with positive rotation and whose diastereomeric amide with D-(+)-1-phenylethyl amine which eluted later in the HPLC system was assigned the S-configuration.

The results are shown in Table 17.

TABLE 17

| Hydrolysis of Indoprofen monoglyceride | | | | | |
|---|---|---|---|---|---|
| Enzyme | Acid (%) | Rate | (S-R) acid (%) | of acid (%) | Observed rotation |
|  |  |  |  |  | Acid / Ester |
| RS-Indoprofen |  |  | 15.8 |  |  |
| Lipase MY (100 mg) | 8.2 | 0.0017 | −35.4 | 51.2 (R) | +.012 / +.005 |
| CSC-2 (10 mg) | 2.3 | 0.0048 | 40.8 | 25.0 (S) | −.007 / −.005 |
| CSC-1 (10 mg) | 1.8 | 0.0037 | −43.8 | 59.6 (R) | +.013 / +.002 |

EXAMPLE 39

The effect of Tween 80 on the hydrolysis of ketoprofen monoglyceride by CSC-2 was demonstrated as follows.

The presence of a surfactant like Tween increases the solubility o lipophilic compounds in water. Experiments were performed to find out if the surfactant could increase the solubility of ketoprofen monoglyceride and to determine its effect on the hydrolysis with CSC-2. In 50ml flasks 1 mg of CSC-2 was dissolved in 10ml of 100mM $(NH_4)H_2PO_4$ (pH 5.5) buffer. Tween 80 was added to make 1% and 2% solution (v/v). Bovine serum albumin (BSA) (10mg) was added to each of two flasks. A solution of 50mg of ketoprofen monoglyceride in 200ul DMF was added to each. After 20 hours at 250 rpm and 35° C. the reaction mixtures were acidified, extracted and analyzed by the usual HPLC procedure as in Example 18. The results are shown in Table 18.

TABLE 18

| Effect of Tween 80 and BSA on Hydrolysis | | |
|---|---|---|
| Reaction | Relative Rate | ee of S-acid (%) |
| No Tween no BSA | 100 | 98 |
| 1% Tween and BSA | 114 | 95 |
| 2% Tween and BSA | 142 | 96 |
| 2% Tween no BSA | 118 | 96 |

EXAMPLE 40

Various surfactants were used at 2% of the reaction volume to determine their effect on the enzymatic reaction involving the conversion of ketoprofen monoglyceride (KPG) to ketoprofen (KP). To Erlenmeyer flasks were added 200 ul of surfactant, 50 mg KPG dissolved in 200 ul DMF, 1 mg of CSC-2 enzyme in 1 ml buffer and 9 ml buffer (100 mM $(NH_4)H_2PO_4$, pH 5.5). Flasks were covered with parafilm and incubated in a 35° C. water bath at 250 rpm, typically overnight. Reactions were stopped by acidification, extracted with $CHCl_3$ (2×10 ml). The %acid and %ee were determined by the method of Example 18. The results of experiments using surfactants are shown below in Table 19. It is to be noted that Hydrophile-Lipophile Balance (HLB) values have no apparent bearing on the ability of the surfactant to enhance the conversion of KPG to KP.

TABLE 19

| Effect of Surfactants on Hydrolysis of Ketoprofen Monoglyceride | | |
|---|---|---|
| Additive | HLB | Relative Rate |
| 0 (enzyme alone, Lipase CSC-2) | — | 100 |
| Arlacel 83 | 3.7 | 172 |
| Brij 35 | 16.9 | 26 |
| Brij 72 | 4.9 | 106 |
| Brij 76 | 12.4 | 18 |
| Brij 78 | 15.3 | 14 |
| Brij 92 | 4.9 | 27 |
| Brij 96 | — | 27 |
| Brij 99 | 15.3 | 15 |
| Igepal CO-210 | 4.6 | 42 |
| Igepal CO-430 | 8.9 | 27 |
| Igepal CO-520 | 10.5 | 25 |
| Igepal CO-530 | 10.9 | 23 |
| Igepal CO-720 | 13.3 | 32 |
| Igepal CO-890 | 17.1 | 30 |
| PEG P1 | — | 98 |
| PEG P4 | — | 96 |
| PEG P11 | — | 69 |
| Pluronic P2010 | — | 79 |
| Pluronic V10 | — | 39 |
| Pluronic P75 | — | 29 |
| Pluronic L64 | — | 33 |
| Pluronic L92 | — | 12 |
| Pluronic F147 | — | 82 |
| Span 20 | 8.6 | 75 |
| Span 40 | 6.7 | 99 |
| Span 60 | 4.7 | 108 |
| Span 80 | 4.3 | 160 |
| Span 85 | 1.8 | 181 |
| Tween 20 | 16.9 | 39 |

TABLE 19-continued

Effect of Surfactants on Hydrolysis of Ketoprofen Monoglyceride

| Additive | HLB | Relative Rate |
|---|---|---|
| Tween 40 | 15.6 | 29 |
| Tween 60 | 14.9 | 23 |
| Tween 61 | 14.9 | 92 |
| Tween 65 | 10.5 | 39 |
| Tween 80 | 15.0 | 136 |
| Tween 85 | 11.0 | 27 |

Of the surfactants referred to above, the Tween series is made up of polyoxyethylene (POE) sorbitans with 20 POE units except for Tween 61 with 5 POE units. The Span series is made up of sorbitans (without POE) with the same numbering sequence. All surfactants listed are from Sigma unless otherwise noted. Tween and Span 20 is monolaurate, 40 is monopalmitate, 60 is monostearate, 61 (Serva) is also a monostearate, 65 (Serva) is a tristearate, 80 is monooleate, and 85 is trioleate. Arlacel 8 is sorbitan sesquioleate. The Brij series is made up of polyoxyethylenes (POE) ethers. Brij 35 is POE-23 lauryl ether, Brij 72 is POE-2 stearyl ether, Brij 76 is POE-10 stearyl ether, Brij 78 is POE-20 stearyl ether, Brij 92 is POE-2 oleyl ether, Brij 96 is POE-10 oleyl ether, and Brij 99 is POE-20 oleyl ether. The Igepal series (GAF) is made up of POE nonylphenol ethers, all consisting of $C_{15}H_{24}O$, with varying amounts (n) of $C_2H_4O$ attached. Igepal CO-210 is $C_{15}H_{24}O-(C_2H_4O)n = 1.5$, CO-430 n=4, CO-520 n=5, CO-530 n=6, CO-720 n=2, and CO-890 n=40. Polyethylene glycol (PEG) dimethyl ethers (Hoechst) used are of length 2000 (P4), 1000 (P1) and 250 (P11). The pluracols and pluronics listed are polyols.

EXAMPLE 41

The effect of oleate ester surfactants on the activity of CSC-2 with ketoprofen monoglyceride was demonstrated as follows:

75 mg of KPG (in the absence of DMF) was individually weighed into 50 ml Erlenmeyer flasks. One mg of CSC-2 in 1 ml buffer was added, as was 100, 200, or 500 ul of oleate ester surfactants, making them 1%, 2%, and 5% of reaction volume. 9 ml of 100 mM $(NH_4)H_2PO_4$, pH 5.5 buffer was added, and the flasks were placed into a 35° C., 250 rpm water bath incubator for 20 hours. The reactions were acidified, extracted with $CHCl_3$ and examined by HPLC as in Example 18. The %ee was determined as per Example 18. The results are shown in Table 20:

TABLE 20

| Additive | % Acid | S-acid |
|---|---|---|
| 0 | 19 | 96 |
| 100 ul Tween 80 | 12 | |
| 200 ul Tween 80 | 22 | 96 |
| 500 ul Tween 80 | 18 | |
| 100 ul Span 85 | 28 | |
| 200 ul Span 85 | 33 | 96 |
| 500 ul Span 85 | 34 | |
| 100 ul Arlacel 83 | 30 | |
| 200 ul Arlacel 83 | 30 | 99 |
| 500 ul Arlacel 83 | 29 | |
| 100 ul Span 80 | 27 | |
| 200 ul Span 80 | 28 | 97 |
| 500 ul Span 80 | 27 | |

EXAMPLE 42

To determine the effects of oleic acid and other esters of oleic acid, an experiment was performed using a protocol similar to Example 41. 50 mg KPG was dissolved in 200 ul of DMF, 1 mg of CSC-2 was added in 1 ml of buffer, and 9 ml of buffer was used. Various amounts of oleic acid or its esters were added, and the reactions stopped at the times indicated, acidified, extracted with $CHCl_3$ and analyzed as in Example 18. The results are shown in Table 21.

TABLE 21

| Time | Additive | % acid | Rate | % ee (S-acid) |
|---|---|---|---|---|
| 18 hr | None | 23 | 2 | ND |
| " | 100 ul triolein | 38 | 3 | ND |
| " | 100 ul Diolein | 42 | 4 | ND |
| " | 100 ul Monolein | 43 | 4 | ND |
| 23 hr | None | 29 | 2 | 96 |
| " | 200 ul oleic acid | 47 | 3 | 96 |
| " | 200 ul oleic acid methyl ester | 51 | 3 | 97 |
| " | 200 ul oleic acid ethyl ester | 52 | 4 | 96 |

ND = Not Determined

EXAMPLE 43

The use of olive oil as an enhancer of CSC-2 activity was shown as follows:

An experiment was performed as in Example 41, but using 100, 200 and 500 ul of olive oil to determine if it would enhance the rate of conversion of KPG to KP. The method was the same as used in Example 41 (50 mg KPG, 1mg CSC-2 in 1 ml buffer, 9ml buffer, olive oil, 35.C, 250 rpm, 20 hours). After 20 hours, all reactions were acidified, extracted with $CHCl_3$ and analyzed by HPLC as in Example 18. The results are given below:

| Additive | % acid |
|---|---|
| None | 19 |
| 100 ul olive oil | 34 |
| 200 ul olive oil | 40 |
| 500 ul olive oil | 42 |

EXAMPLE 44

Olive oil and other oils were used as substrates for hydrolysis by CSC-2 as follows:

Olive oil (1 g) was suspended in 10 ml of 100 mM ammonium phosphate buffer (pH 5.5). A solution of 1 mg of CSC-2 in 1 ml of the same buffer was added and the mixture was shaken at 250 rpm at 35° C. for 1 hour. The reaction was terminated by the addition of 10 ml of a mixture of acetone and methanol (1:1), diluted with 50 ml of water and titrated with a standard solution of sodium hydroxide using phenolphthalein as indicator. The result was then compared with the control reaction without the enzyme. The enzyme reaction produced 1.31 mmole of acid in one hour.

Other natural triglycerides were tested as substrates of Lipase MY, CSC-1, and CSC-2. 200 ul of each oil was placed in a scintillation vial with enzyme (1 mg of CSC-1 or CSC-2 or 50 mg of Lipase MY) in 2 ml of buffer (100 mM $(NH_4)H_2PO_4$, pH 5.5). Some flasks also received 20-30 mg of ketoprofen monglyceride (KPG). Oleic acid was also used as a substrate for transesterification. After an overnight incubation at 35C, 250 rpm, the reactions were analyzed by thin layer chromatography (TLC) using silica gel plates. The solvent system was 95:5 $CHCl_3:CH_3OH$. Plates were visualized with iodine vapor. In other experiments it was found that myristic acid (C14), palmitic acid (C16), and stearic acid (C18) are difficult to detect under these conditions, and of the C18 unsaturated fatty acids, oleic, linoleic, and linolenic do not separate well. The conditions and results (presence of spots corresponding to C18 unsaturated fatty acids, tri, di and mono glyceride esters of oleic acid) using olive oil, corn oil, and oleic acid as substrates are given in Table 22.

TABLE 22

| Substrate: | Olive oil | | | | corn oil | | | | oleic acid | | | |
| --- | --- | --- | --- | --- | --- | --- | --- | --- | --- | --- | --- | --- |
| | C18 | tri | di | mono | C18 | tri | di | mono | C18 | tri | di | mono |
| substrate alone | | + | | | | + | | | + | | | |
| substrate + CSC-2 | + | + | + | + | + | + | + | + | + | | | |
| substrate + CSC-2 + KPG | + | | | | + | | | | + | + | + | + |
| substrate + CSC-1 | + | + | + | + | + | | | | + | | | |
| substrate + CSC-1 + KPG | + | + | + | + | + | + | | + | + | + | + | + |
| substrate + Lipase MY | + | + | + | + | + | + | | | + | | | |
| substrate + Lipase MY + KPG | + | + | + | + | + | + | + | + | + | + | + | + |

EXAMPLE 45

To determine the effect of other naturally occurring oils (triglyceride esters of oleic and other acids), on the CSC-2 hydrolysis of ketoprofen monoglyceride a series of experiments were performed. 50 mg of KPG was weighed into Erlenmeyer flasks. 1 mg of CSC-2 in 1 ml 100 mM $(NH_4)H_2PO_4$ pH 5.5 buffer and 20 ul oil were added, along with 9 ml buffer. Flasks were incubated at 35° C., 250 rpm for 23 hours. The reactions were stopped by acidification, extracted with $CHCl_3$, and analyzed by HPLC as in Example 18. The additive is listed along with its percentage composition of glycerides of oleic acid. The following results were obtained:

TABLE 23

| Additive | % Oleates in oil | % Acid | ee (S-acid) |
| --- | --- | --- | --- |
| 0 | | 32 | 97 |
| 20 ul corn oil | 43 | 41 | 96 |
| 20 ul peanut oil | 42–61 | 42 | 96 |
| 20 ul soybean oil | 23–31 | 41 | 96 |
| 20 ul lard oil | 38–44 | 40 | 96 |
| 20 ul olive oil | 64–84 | 41 | 96 |

EXAMPLE 46

Preparation of S-ketoprofen in the presence of additives.

To determine the problems associated with having oleic acid or oleate, esters in the reaction media, the following experiment was performed. To 250 ml Erlenmeyer flasks were added 5 g KPG, 50 mg of CSC-2 enzyme, and 5 grams of oleates (oils or oleic acid). Flasks were placed in a 35° C. incubator at 250 rpm, and the reactions were sampled by taking 200 ul aliquots at various time points. These aliquots were analyzed by HPLC (ODS-3 RAC column, $CH_3OH$: 10 mM $(NH_4)H_2PO_4$ (60:40) eluant, 4 ml/min, 254 nm detection) to determine the course of reaction. When approximately 40% acid was produced, the reactions were stopped by placing the flasks in the −70° C. freezer. Two extraction procedures were utilized to determine the best method of isolating S-Ketoprofen free of oleic acid. The first (listed as Extraction Procedure I in the following table) involved first making the solution basic (pH 10) with NaOH, then extracting with hexane, then $CHCl_3$. The aqueous layer was then acidified to pH 1.5 with HCl, extracted with hexane, then $CHCl_3$. Fractions containing ketoprofen acid were then pooled, extracted in to $CHCl_3$, and the ketoprofen acid removed with 5% $NaHCO_3$. This was then extracted into $CHCl_3$, evaporated, and crystallized using ethanol. As noted in the following table (Table 24), the oleic acid was not separated completely from the ketoprofen. The other flasks were extracted using Extraction Procedure II. The solutions were first made acidic (pH 1.5) with 6N HCl, and the ketoprofen acid and ester extracted with $CHCl_3$. The ketoprofen acid was then removed with 5% $NaHCO_3$, which was then acidified and extracted into $CHCl_3$. The $CHCl_3$ was evaporated, and the ketoprofen was recovered. By TLC on silica plates using 95:5 $CHCl_3:CH_3OH$ and iodine vapor development, as well as by NMR, the ketoprofen acid was found to contain <5% oleic acid. The results are given in Table 24:

TABLE 24

| Procedure | % Acid | Final Rate uMole/hr/mg | Isolated Acid (g) | Isolated % ee (S-Acid) | Extraction |
| --- | --- | --- | --- | --- | --- |
| CSC-2 alone | 40.5 | 0.53 | 0.86 | 95.8 | II |
| + Olive oil | 37 | 1.1 | 1.07 | 95.4 | II |
| + Oleic acid | 39 | 1.2 | ? | 88. | I |
| + Corn oil | 31 | 0.95 | ? | 84.8 | I |
| + Tween 80 | 34.9 | 0.46 | 0.78 | 94.3 | II |
| + Span 85 | 28.9 | 0.87 | 0.84 | 95.1 | II |

EXAMPLE 47

This example illustrates the effect of mineral oil on ketoprofen monoglyceride hydrolysis by CSC-2.

To determine if there was a non-specific enhancing effect of paraffin oils on the rate of conversion of KPG to KP by CSC-2, the enzymatic hydrolysis procedure of Example 44 was repeated. In this experiment, mineral oil was used at 2% of reaction volume. The reactions were stopped at 23 hours, acidified, extracted with $CHCl_3$ and analyzed by HPLC as in Example 18. No significant increase in the rate of acid production was observed using mineral oil.

| | % Acid |
| --- | --- |
| CSC-2 | 29 |

-continued

|  | % Acid |
|---|---|
| CSC-2 — 200 ul mineral oil | 30 |

EXAMPLE 48

This example illustrates the specificity of reaction rate enhancement of CSC-2 using oleic acid.

To determine the effect of compounds closely related to oleic acid and its esters (in addition to the surfactants already mentioned), a series of experiments were performed as in Example 40, including the use of 200 ul of DMF to solubilize the substrate. The reactions were stopped at the times indicated, acidified, extracted with CHCl$_3$ and analyzed by HPLC as in Example 18 with the following results:

TABLE 25

| Time (hr) | Additive | % Acid |
|---|---|---|
| 18 | 0 | 23 |
| " | 200 ul Triacetin | 12 |
| " | 100 ul tributyrin | 3 |
| 23 | 0 | 29 |
| " | 200 ul linoleic acid | 21 |
| " | 200 ul linoleic acid methyl ester | 34 |
| " | 200 ul Linoleic acid ethyl ester | 26 |
| " | 100 ul dilinolein | 20 |
| " | 100 ul trilinoein | 20 |
| 23 | 0 | 32 |
| " | 25 ul monostearin | 31 |
| " | 25 ul distearin | 30 |
| " | 28 ul tristearin | 25 |
| " | 200 ul linolenic acid | 13 |

EXAMPLE 49

This example illustrates the rate enhancement effect of oleic acid on Lipase MY, CSC-1 and CSC-2.

To determine which enzyme in the Lipase MY preparation responds to oleic acid and its esters by enhancement of the rate of conversion of ketoprofen esters, particularly ketoprofen monoglyceride, to ketoprofen, 50 mg of KPG in the absence of DMF was weighed into a flask to which was added either 1 mg of CSC-2 in 1 ml buffer, 1 mg CSC-1 in 1 ml buffer, or 50 mg Lipase MY in 1 ml buffer. 9 ml buffer (100 mM (NH$_4$)H$_2$PO$_4$ pH 5.5) was added and 200 ul oleic acid was added to some of the flasks. The flasks were incubated at 35° C., 250 rpm, for 21 hours. The reactions were stopped by acidification and CHCl$_3$ extraction and analyzed by HPLC as in Example 18.

The results shown in Table 26 were obtained:

TABLE 26

| Enzyme | Additive | % Acid | % ee (S acid) |
|---|---|---|---|
| 50 mg Lipase MY | 0 | 31 | 81 |
|  | 200 ul oleic acid | 46 | 83 |
| 1 mg CSC-1 | 0 | 6 | 85 |
|  | 200 ul oleic acid | 5 | 84 |
| 1 mg CSC-2 | 0 | 33 | 97 |
|  | 200 ul oleic acid | 52 | 97 |

EXAMPLE 50

This example demonstrates the effect of oleic acid on the rate of hydrolysis of various ketoprofen esters by Lipase MY and Candida lipase B (Biocatalyst).

Since oleic acid enhanced the rate of conversion of KPG to KP by Lipase MY and CSC-2, a series of esters of ketoprofen were used. This experiment compared oleic acid enhancement of the rate of conversion of different esters of ketoprofen by either Lipase MY or the Candida lipase B (Biocatalyst). Ketoprofen ester (50 mg) was placed in an Erlenmeyer flask, and 50 mg of Lipase MY or Biocatalyst Lipase (repeated in one case listed at 10 mg, 16 hrs) was added in 1 ml buffer, as was 9 ml buffer. Oleic acid (200 ul) was added to some flasks. The reactions were incubated at 35° C., 250 rpm, for 17 hours, acidified, extracted with CHCl$_3$, and analyzed by HPLC. The data is given below in Table 27.

TABLE 27

|  | Lipase MY | | Candida Lipase B | |
|---|---|---|---|---|
| Ketoprofen ester Substrate | Alone % acid | + Oleic % acid | Alone % acid | + Oleic % acid |
| methyl | 4 | 4 | 14 | 15 |
| n-propyl | 15 | 13 | 43 | 33 |
| n-hexyl | 4 | 7 | 26 | 15 |
| 2,2,2-trichloroethyl | 34 | 13 | 41 | 39 |
| monoglyceride | 23 | 40 | 44* | 53* |

*10 mg, 16 hrs

EXAMPLE 51

This example describes the improvement in stereoselectivity and rate of reaction by oleic acid using the 2-chloroethyl ester of ketoprofen.

An experiment was performed using 50 mg of the 2-chloroethyl ester of ketoprofen (in the absence of DMF). The enzymes used were 50 mg of Lipase MY or 50mg of Candida lipase B (Biocatalyst) or 1 mg each of CSC-1 or CSC-2, dissolved in 1 ml of buffer. Oleic acid was used at 200 ul, and 9 ml of buffer was added. The reactions were incubated at 35° C., 250 rpm, for 15.5 hours, acidified and extracted with CHCl$_3$. The analysis was carried out as performed in Example 18. The data obtained is set forth in Table 28.

TABLE 28

| 2-Chloroethyl Ester of Ketoprofen | | | |
|---|---|---|---|
| Enzyme | Additive | % Acid | % ee S-acid |
| 50 mg Lipase MY | 0 | 12 | 21 |
|  | 200 ul oleic acid | 20 | 87 |
| 1 mg CSC-2 | 0 | 12 | 93 |
|  | 200 ul oleic acid | 26 | 99 |
| 1 mg CSC-1 | 0 | 4 | 89 |
|  | 200 ul oleic acid | 2 | 55 |
| 50 mg Candida Lipase B | 0 | 8 | 25 |
|  | 200 ul oleic acid | 9 | 85 |

EXAMPLE 52

This example describes the effect of oleic acid on the reaction rate and stereospecificity of other enzymes and other esters of ketoprofen.

To determine whether oleic acid could be used to enhance the rate/selectivity using other lipase and/or substrates, the following experiment was performed. 50 mg of either the diethylene glycol ester, triethylene glycol monomethyl ester, monoglyceride ester, or ethylene glycol ester was placed in 50 ml Erlenmeyer flasks. To this was added 50 mg of Lipase MY, 50 mg of the Mucor miehei lipase, 2.5 mg of the *Candida cylindracea* lipase (Biocatalyst), or 5 mg of lipase OF, all in 1 ml of buffer. 10 ul of pig liver esterase was also used. Oleic acid was added to the flasks at 200 ul. Buffer was added to a final volume of 10 ml. and the flasks were incubated at 35.C, 250 rpm, acidified, and extracted with CHCl₃ and analyzed by HPLC as in Example 18. The data obtained is presented in Table 29:

TABLE 29

|  | Diethylene Glycol Ester of Ketoprofen | | Monomethyl Triethylene Glycol ester of ketoprofen | | Monoglyceride Ester of ketoprofen | | Ethylene Glycol Ester of ketoprofen | |
| --- | --- | --- | --- | --- | --- | --- | --- | --- |
|  | % Acid | % ee | % Acid | % ee | % Acid | % ee | % Acid | % ee |
| Lipase MY + | 38 | 48 | 16 | 62 | 18 | 70 | 9 | 60 |
| Oleic | 41 | 66 | 16 | 81 | 37 | 82 | 27 | 95 |
| Mucor miehei + | 24 | 41R | 26 | 36R | 20 | 40R | 17 | 54R |
| Oleic | 20 | 2R | 6 | 1R | 4 | 35R | 10 | 42R |
| Pig Liver Esterase + | 11 | ? | 20 | 2R | 10 | 36R | 3 | 51R |
| Oleic | 5 | 8 | 5 | 15 | 1 | 14R | 3 | 64R |
| Biocatalyst Candida Lipase + | 24 | 54 | 9 | 60 | 19 | 57 | 7 | 47 |
| Oleic | 33 | 53 | 10 | 70 | 34 | 78 | 25 | 91 |
| Lipase OF + | 40 | 39 | 17 | 61 | 35 | 41 | 13 | 31 |
| Oleic | 48 | 60 | 18 | 81 | 48 | 69 | 39 | 88 |

EXAMPLE 53

This example describes the oleic acid enhancement of hydrolysis of ketoprofen esters with free or immobilized enzyme.

200 mg of either KPEG or KPG was added to an Erlenmeyer flask, to which was added 1 mg of free CSC-2 in 1 ml buffer or 200 mg of CSC-2 immobilized on Silica gel (279-SD1) as per Example 24, run 16 (determined to be equivalent to 1 mg free enzyme). Oleic acid was added at 0, 50, 200, 500, or 1000 ul, and buffer added to a final reaction volume of 10 ml. The reactions were stopped between 14 and 21 hours by acidification and CHCl₃ extraction, and % acid and %ee determined as in Example 18. The results obtained are set out in Table 30.

TABLE 30

| Enzyme | Substrate | Oleic acid (ul) | % Acid | % ee (S-acid) |
| --- | --- | --- | --- | --- |
| Immobilized CSC-2 | Ethylene Glycol Ester of ketoprofen | 0 | 2 | 95 |
|  |  | 50 | 2 | 95 |
|  |  | 200 | 5 | 97 |
|  |  | 500 | 11 | 97 |
|  |  | 1000 | 18 | 98 |
| Free CSC-2 | Ethylene Glycol Ester of ketoprofen | 0 | 3 | 93 |
|  |  | 50 | 5 | 97 |
|  |  | 200 | 12 | 98 |
|  |  | 500 | 28 | 97 |
|  |  | 1000 | 33 | 97 |
| Immobilized CSC-2 | Monoglyceride ester of ketoprofen | 0 | 1 | 87 |
|  |  | 50 | 2 | 92 |
|  |  | 200 | 4 | 93 |
|  |  | 500 | 5 | 92 |
|  |  | 1000 | 7 | 92 |
| Free CSC-2 | Monoglyceride ester of ketoprofen | 0 | 1 | 91 |
|  |  | 50 | 3 | 93 |
|  |  | 200 | 9 | 95 |
|  |  | 500 | 15 | 94 |
|  |  | 1000 | 21 | 96 |

EXAMPLE 54

This example demonstrates the effect of oleic acid, hexane and water on the production of ketoprofen by CSC-2.

To determine whether transesterification was possible without enzymatic hydrolysis, and also to avoid the problems inherent in a multiphase system of oleic acid and aqueous buffer, the enzymatic conversion of ketoprofen esters to ketoprofen was attempted in hexane and oleic acid mixed at various ratios. In this experiment, KPEG was used at 200mg, immobilized CSC-2 on Silica (279-SD1), as in Example 53 above, used at 200 mg (equivalent to 1 mg free enzyme), and hexane and oleic acid were used at various levels (from 10 ml and 0 ml each to 0 ml and 10 ml each). Buffer was added to some flasks at 50 ul (0.5% of reaction volume). Flasks were incubated at 35° C., 250 rpm, and a 200 ul aliquot taken at 17.5 hours, diluted into methanol, and injected on the HPLC directly. The standard ODS-3 RAC column with CH₃OH:10mM (NH₄)H₂PO₄ (60:40) eluate at 4 ml/min and detection at 254nm was used. The data is given below in Table 31:

TABLE 31

| Hexane (ml) | Oleic acid (ml) | Buffer (ul) | % Acid | Rate uMole/hr/mg |
| --- | --- | --- | --- | --- |
| 10 | 0 | 0 | 1 | <1 |
| 10 | 0 | 50 ul | 0 | 0 |
| 8 | 2 | 0 | 18 | 6 |
| 8 | 2 | 50 ul | 15 | 5 |
| 2 | 8 | 0 | 5 | 2 |
| 2 | 8 | 50 ul | 13 | 4 |
| 0 | 10 | 0 | 5 | 2 |
| 0 | 10 | 50 ul | 10 | 4 |

EXAMPLE 55

This example describes the effect of organic solvents on the production of ketoprofen.

To optimize the organic solvent used in the presence of oleic acid a variety of organic solvents were used, along with a variety of ketoprofen esters. In this experiment, 50 mg of ketoprofen esters were weighed into flasks, along with 1 ml of oleic acid and 9 ml of an organic solvent. The flasks were capped and incubated at 35° C., 250 rpm, for 10–26 hours before stopping the reaction by first adding 4 ml CHCl₃ to solubilize the substrates and products, then filtering through a 0.2 um Gelman Nylaflo filter. Samples were then diluted in methanol and analyzed by HPLC as in Example 18. The experiment was also performed using 200 ul of oleic acid and 10ml buffer, which was acidified, extracted with CHCl₃ and analyzed by HPLC as above. The data are below in Table 32:

TABLE 32

| Ketoprofen ester | Buffer 10 ml OA 200 ul | | Hexane 9 ml OA 1 ml | | Toluene 9 ml OA 1 ml | | Isooctane 9 ml | | | | CHCl₃ 9 ml | |
|---|---|---|---|---|---|---|---|---|---|---|---|---|
| | | | | | | | OA 1 ml | | OA 1 ml | | | |
| | % acid | (% ee) | % acid | (% ee) | % acid | (% ee) | % acid | | (% ee) | | % acid | (% ee) |
| Ethylene Glycol Ester | 21 | (98) | 29 | (95) | 0 | | 47 | | (98)* | | 0 | |
| Monoglyceride Ester | 26 | (96) | 47 | (97) | 0 | | 31 | | (96) | | 0 | |
| 2-Chloroethyl Ester | 18 | (96) | 7 | (92) | 1 | (<1%) | 18 | | (97) | | 2 | (3) |
| Diethylene glycol ester | 32 | (30) | 56 | (13)* | N.D. | | 60 | | (17)* | | N.D. | |
| Methyl ester | 2 | (96) | 0.8 | | 0 | | 2 | | (93) | | 0 | |

*Reaction stopped at 10 Hr
ND — Not Determined
OA — Oleic Acid

EXAMPLE 56

Since KPG and KPEG seemed to be the most effective esters in organic solvents, an experiment was performed using KPG and KPEG as substrates with a variety of different organic solvents or buffer, all in the presence of 1 ml of oleic acid. 50 mg of either KPG or KPEG were weighed into Erlenmeyer flasks, as was 100 mg CSC-2 immobilized on Silica (279-SD-1), equivalent to 0.5 mg free enzyme. One ml of oleic acid was added, as was 9 ml of buffer (100 mM (NH₄)H₂PO₄, pH 5.5) or organic solvent. Flasks were placed into a 35° C. incubator and shaken at 250 rpm for 13 hours. Reaction was stopped by adding 5 ml CHCl₃ to solubilize the organic material and filtering the solutions using 0.2 um Gelman Nylaflo membranes to remove the enzyme. Samples were analyzed on an ODS-3 RAC column using CH₃OH:10 mM (NH₄)H₂PO₄ (60:40) as eluant, flow rate 4 ml/min, and detection at 254 nm. %ee was determined by the resolution of diastereomeric amides on the above HPLC system, as per Example 18. The results are given in Table 33:

TABLE 33

| | Monoglyceride Ester of ketoprofen | | Ethylene glycol ester of ketoprofen | |
|---|---|---|---|---|
| Solvent 9 ml/1 ml | % Acid | % ee S-acid | % Acid | % ee S-acid |
| Buffer/Oleic acid | 17 | 97 | 19 | 97 |
| Hexane/Oleic acid | 12 | 94 | 16 | 87 |
| Isooctane/Oleic acid | 39 | 98 | 48 | 97 |
| Cyclohexane/Oleic acid | 38 | 98 | 29 | 83 |
| Cyclohexene/Oleic acid | 12 | 94 | 3 | 52 |
| Cyclooctene/Oleic acid | 38 | 98 | 16 | 92 |
| Tetrahydronaphthalene/ Oleic acid | 2 | 68 | 1 | 1 |
| 1,1,1, Trichloroethane/ Oleic acid | 1 | 0 | 0 | 0 |
| Tetrachloroethylene/ Oleic acid | 1 | 0 | 0 | 0 |

EXAMPLE 57

Another lipase from *C. rugosa*, Enzeco Rxx, available from Enzyme Development Corporation was evaluated by SDS-PAGE and IEF. The SDS-PAGE showed the molecular weight of Enzeco Rxx to be slightly higher than CSC-2 (FIG. 12). However, the IEF showed a major band at the same isoelectric point as CSC-2.

Evaluation of the Enzeco Rxx activity with KPG or KPEG (50mg) in 10ml of 100mM NH₄H₂PO₄, pH 5.5 buffer with and without the addition of 200 ul of oleic acid for an incubation period of 18 hours at 35° C. and 750 RPM gave the results shown in Table 34.

TABLE 34

| Enzyme | Oleic Acid Added | KPG | | | KPEG | | |
|---|---|---|---|---|---|---|---|
| | | % Acid Formed | Rate (uMole/hr/mg) | % ee S-acid | % Acid Formed | Rate (uMole/hr/mg) | % ee S-acid |
| CSC-2 | 200 ul | 44 | 4 | 98 | 60 | 5 | 97 |
| CSC-2 | 0 | 75 | 1 | 95 | 20 | 2 | 93 |
| Enzeco Rxx | 200 ul | 33 | 3 | 66 | 36 | 3 | 83 |
| Enzeco Rxx | 0 | 33 | 3 | 22 | 20 | 20 | 19 |

EXAMPLE 58

This example describes the separation and purification of the isozymes of lipase MY using isoelectric focusing.

Figure 13:
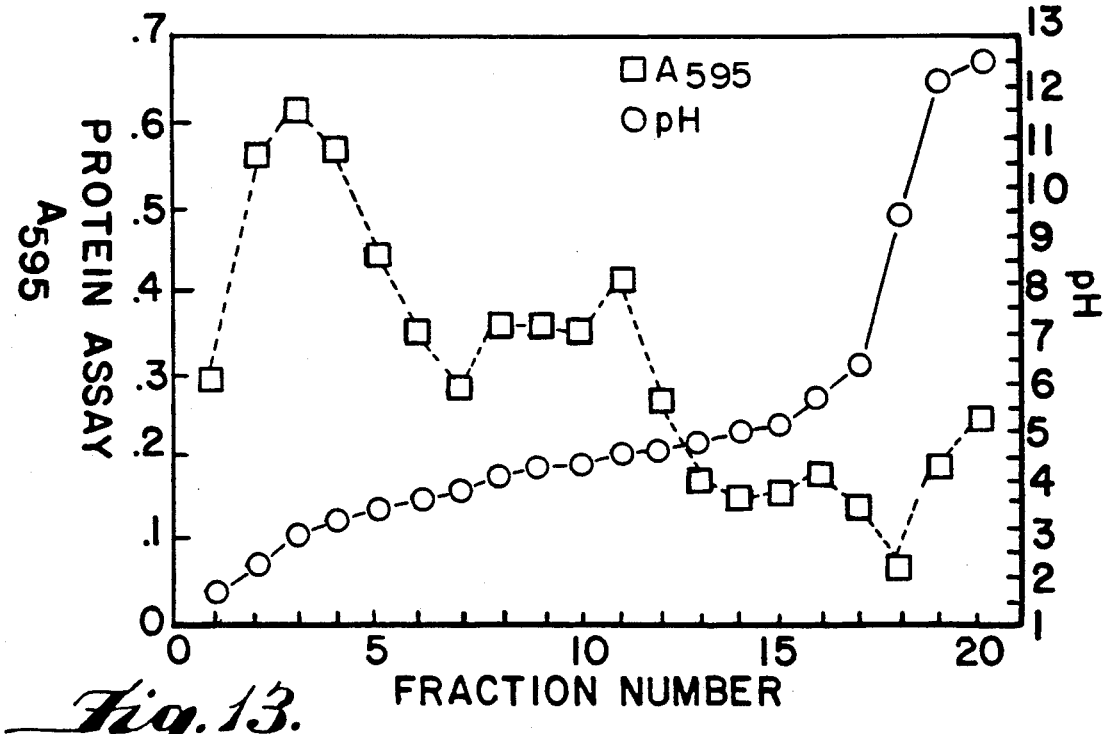

As an alternative method to the use of ion-exchange columns, a preparative isoelectric focusing (IEF) cell was used to separate the isozymes of lipase MY on the basis of their individual charges. Lipase MY that had been previously desalted on a Trisacryl GF-05 column was lyophilized and 400 mg was dissolved into 50 mls deionized water with 2 mls of pH 2.5-5 ampholytes. This sample was placed in the preparative IEF cell and focused at 12 watts at 4° C. for 4 hours. Voltage and current were effectively unlimited (3000 volts and 150 mamps maximum). After 4 hours, samples were harvested by vacuum aspiration, and their pH and protein content determined without any dialysis (to remove ampholytes) of the fractions. The results are shown in the graph of FIG. 13. A pH 3-9 analytical IEF gel of the fractions showed the separation of lipase CSC-2 (fractions 8-12) and lipase CSC-1 (fractions 13-17) that was obtained. As a demonstration of the activity of the fractions, 1 ml each of certain fractions were assayed for stereospecific hydrolytic activity in aqueous buffer against 50 mg of the monoglyceride ester of ketoprofen in the presence or absence of 200 ul of oleic acid as per the method of Example 18. The activity and %ee of the fractions are presented in Table 35 below.

TABLE 35

| pH | Fraction % | Acid | % ee (S-acid) |
|---|---|---|---|
| 3.9 | 2 | 3 | 63 |
|  | 2 + oleic | 6 | 86 |
| 4.15 | 4 | 8 | 92 |
|  | 4 + oleic | 23 | 96 |
| 4.1 | 5 | 4 | 85 |
|  | 5 + oleic | 14 | 94 |
| 4.2 | 7 | 8 | 90 |
|  | 7 + oleic | 30 | 96 |
| 4.3 | 9 | 18 | 96 |
|  | 9 + oleic | 43 | 98 |
| 4.4 | 11 | 11 | 95 |
|  | 11 + oleic | 40 | 97 |

EXAMPLE 59

This example illustrates the use of Lipase AY for the preparation of CSC-1 and CSC-2.

Lipase AY 30 (Amano) was solubilized in 40 mls of deionized water and dialyzed in a 2000 m.w. cutoff dialysis bag, 2 times in 10L of deionized water for 18 hours. The retained material was centrifuged at 7500 RPM for 20 minutes and the pellet was discarded. The supernatant was then chromatographed on a SP-Trisacryl M ion exchange resin (13×25 cm column). The SP-Trisacryl M column was pre-equilibrated with 25 mM sodium acetate pH 3.3. The supernatant was loaded at 50 ml/hr; the column was washed with equilibration buffer to baseline and eluted with 25 mM acetate buffer at pH 4.6, followed by elution with 25 mM acetate buffer at pH 6.4. The fractions collected during the run were analyzed by IEF. CSC-1 and CSC-2 were isolated effectively using this procedure.

EXAMPLE 60

This example further illustrates that the stereoselectivity of Lipase MY is increased by immobilization and use.

Lipase MY 150 mg, free or immobilized, was assayed in 10 ml of pH 7 buffer and 5 ml of 1M HPPA-Me. The immobilized enzyme was more selective. However, the hydrolysis did not stop after the R ester was completely consumed.

TABLE 36

| | Free Enzyme vs. Immobilized Enzyme | | |
|---|---|---|---|
| Time (hrs) | Free % R (% Conv) | XAMA-2 % R (% Conv) | XAMA-7 % R (% Conv) |
| 4 | 73(16) | 87(15) | 84(17) |

EXAMPLE 61

Reaction Conditions

Substrate, 400 mg of (R,S)-HPPA-Me, was placed in a 500 ml Erlenmeyer flask and 200 ml of 0.20 M KH$_2$PO$_4$ (pH 6.5) buffer was added followed by 0.3 g of Lipase MY. The mixture was shaken at 250 RPM in Dubnoff shaker at room temperature (25° C.) for 21.5 hours. Samples were taken at 0.5 hr intervals from 0–6.5 hrs and then at 21.5 hrs for analysis.

Optimization of pH (R,S)-HPPA-Me, 196 mg, was added to a series of 100 ml of phosphate buffer solutions ranging from pH 4 to 8.5 in 0.5 unit increments in a 250 ml flasks. The mixtures were shaken for 20 minutes to solubilize the ester. A 1 mg/ml solution of lipase MY was prepared, centrifuged at 7500 RPM for 20 minutes and 0.5 ml of this supernatant was added to each flask. The flasks were placed in a Dubnoff shaker at room temperature and sampled at 7 hours to determine the percent conversion of(R,S)-HPPA-Me to (R)-HPPA and the enantiomeric purity of the final product.

The Effect of High Concentrations of (R,S)-HPPA-Me (R,S)-HPPA-Me (1.5 moles) was combined with 1 liter of 0.5 M phosphate buffer, pH 7.0. The temperature of the reaction was controlled at 40°–45° C. in a water bath and 1 g of lipase MY was then added. The reaction was stirred mechanically for 114 hours and samples were taken at various intervals to determine the enantiomeric purity and concentration of the (R)-HPPA produced.

Optimum Temperature (R,S)-HPPA-Me, 294 g, was placed in a 2L Erlenmeyer flask with 1 L of 1M ammonium acetate, pH 7.05, 150 ml of toluene and 2g of Lipase MY. The temperature of the reaction was maintained at 12°, 21°, 35°, or 45° C. via a chilled water bath or a heated water bath. Samples of the aqueous layer were withdrawn at intervals to determine the total concentration of HPPA produced and the relative amounts of (R)- and (S)-HPPA.

Product Inhibition

A. Inhibition of activity by the alcohol produced upon hydrolysis

Two hydrolysis reactions were run to determine the effect of methanol, produced as a by-product of the hydrolysis of HPPA-Me, on the activity of Lipase MY. (R,S)-HPPA-Me, 1.5 moles, 1 L of 1 M NH$_4$OAc, pH 6.5, 150 ml toluene, and 2 g Lipase MY were placed in flasks with and without 0.75 moles of methanol. The mixtures were shaken gently and sampled at various times to determine the concentrations of each of the stereoisomers of HPPA which were produced.

B. Inhibition of activity by (R)-HPPA

To determine the effect of the (R)-HPPA produced during the hydrolysis of (R,S)-HPPA-Me on the activity of Lipase MY, a series of three experiments were performed. Ammonium acetate, 200 ml, 0.04 M, pH 7.0, was combined with 30 ml of toluene, 40 mmoles (R,S)-HPPA-Me, 25 mg Lipase MY, and 0, 30, or 100 mM (R)-HPPA. The reactions were shaken gently for 136 hours and sampled at various times to determine the concentrations of each of the stereoisomers of HPPA which were produced.

C. Effect of Dilution

To determine the effect of substrate concentration on the activity of Lipase MY, reactions containing 25, 175, or 375 ml of water, 0.04 moles HPPA-Me, 0.04 moles ammonium acetate (pH adjusted to 7.0), 30 ml of toluene and 25 mg Lipase MY dissolved in 25 ml of water were carried out. The reactions were shaken for 164 hours. Samples of the aqueous layer were analyzed at various time intervals to determine the concentrations of each of the stereoisomers of HPPA which were produced.

Kilogram Scale Reaction

Lipase MY, 25 g, in 1 L of 0.2 N ammonium acetate, pH 6.5, was stirred for 20 minutes, centrifuged at 10,000×g and the supernatant added to 1.176 kg of (R,S)-HPPA-Me in 9 L of water, 2.5 L of toluene and the mixture was stirred gently for 29 hours. Samples were taken periodically and analyzed by HPLC. At the end of the reaction, the aqueous phase was drawn off and extracted with $CH_2Cl_2$. The aqueous phase was then adjusted to pH 2.1 and extracted with ethyl acetate. Magnesium sulfate was added to remove traces of water. The ethyl acetate was removed under vacuum and the product was obtained as a light tan powder.

Results

Figure 14:
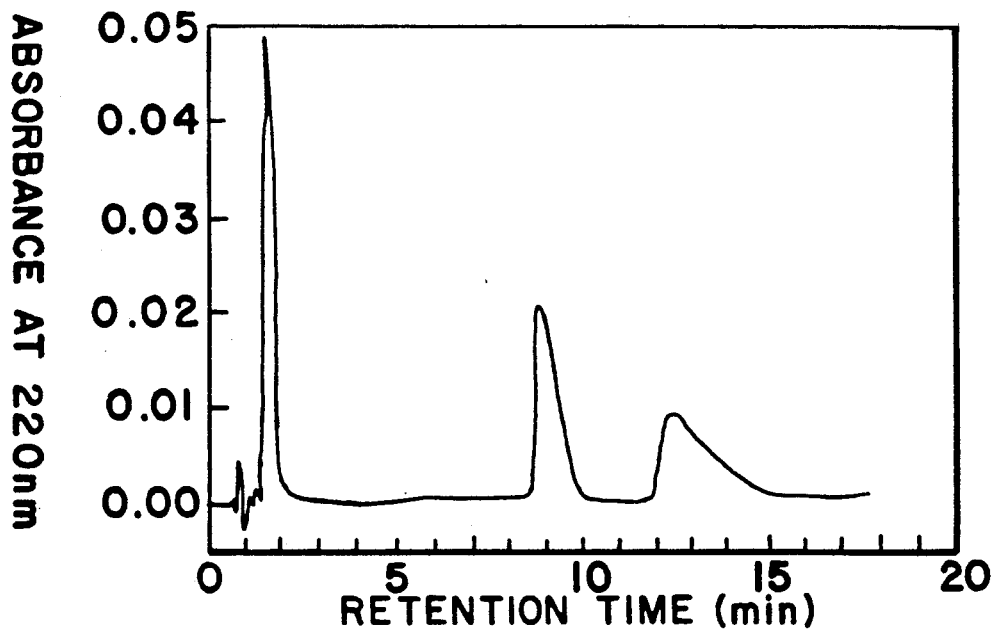

The HPLC conditions given provided baseline separation of the ester and each of the enantiomeric acids (FIG. 14). (R,S)-HPPA-Me eluted at 1.3 min, (R)-HPPA eluted at 8.8 min and (S)-HPPA eluted at 12.4 min.

Under the initial reaction conditions an optical purity of 88% ee was obtained after 35% hydrolysis of (R,S)-HPPA-Me.

Figure 15:
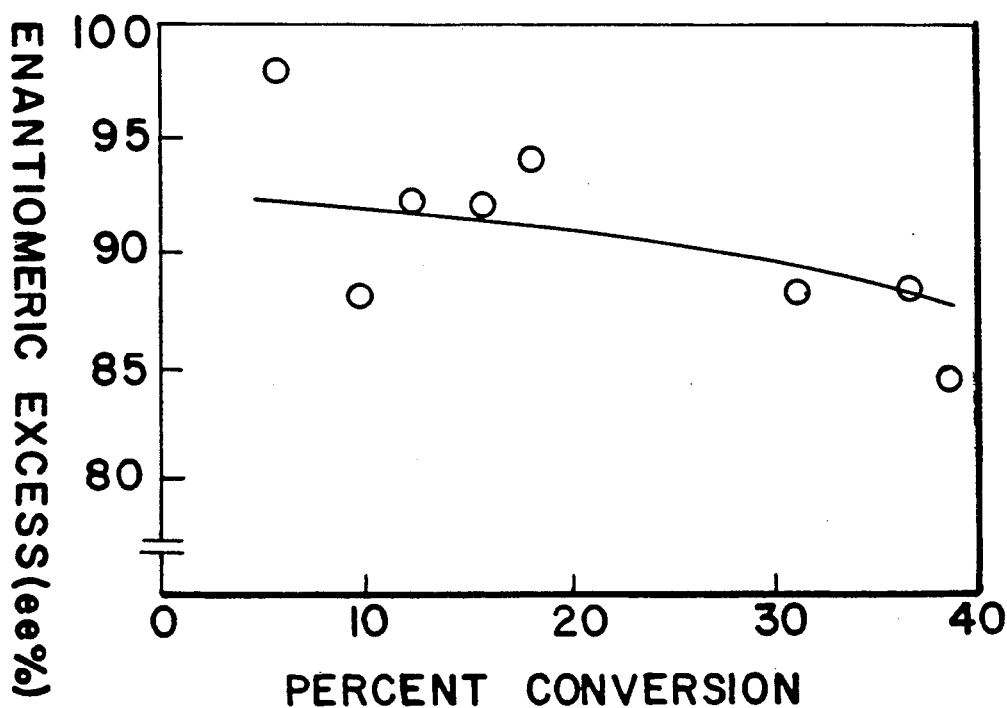

The effect of pH on the rate of hydrolysis and enantiospecificity is given in Table 37. The optimum pH for the rate of enzymatic hydrolysis was at 8.0, where a 51% conversion was achieved after 7 hours reaction time (146.6 uM/hr/mg). The rate optimum was fairly broad with hydrolysis rates being nearly the same over the range of 6.5 to 8.5. The optimum pH for enantioselectivity occurred at pH 3-4, where the ee was 88% for (R)-HPPA. The activity at these pH levels was low, however. All further experiments were run at pH 6.5, in order to maintain adequate activity and enantiomeric purity. Controls without enzyme showed that pH values above 7 resulted in increased chemical hydrolysis of (R,S)-HPPA-Me and decreased enantiomeric purity. The enantiomeric purity of the HPPA produced also decreases as the percent conversion approaches 50% (FIG. 15). This is due to incomplete specificity of Lipase MY for the HPPA-Me substrate.

An experiment was performed to determine what effect a saturated aqueous solution of (R,S)-HPPA-Me had on the activity of enzyme and the enantiomeric purity of the product. The solubility of HPPA-Me is less than 25 mM at pH 6.5 in aqueous solution, whereas HPPA has a high solubility in aqueous solution at pH 6.5. Both the enantioselectivity and activity of the enzyme suffered when the solution was saturated with (R,S)-HPPA-Me. The enantioselectivity of the enzyme in a (R,S)-HPPA-Me saturated solution was completely destroyed. The activity of the enzyme in 25 mM (R,S)-HPPA-Me substrate at 4% conversion was 6.5 mmols/hr/mg. Compared to the saturated substrate data (Table 38), the activity was 6.5 times higher with a 25 mM solution of HPPA-Me.

The optimum temperature for enzymatic hydrolysis of (R,S)-HPPA-Me at pH 7.0 and 20% hydrolysis, was found to be 21° C. (Table 39). The initial activity is substantially higher at 35° C. or 45° C., as expected, however, the activity dropped off quickly indicating enzyme inactivation. There was no variation in the enantioselectivity of the enzyme based on differences in the temperature of the reaction.

Figure 16:
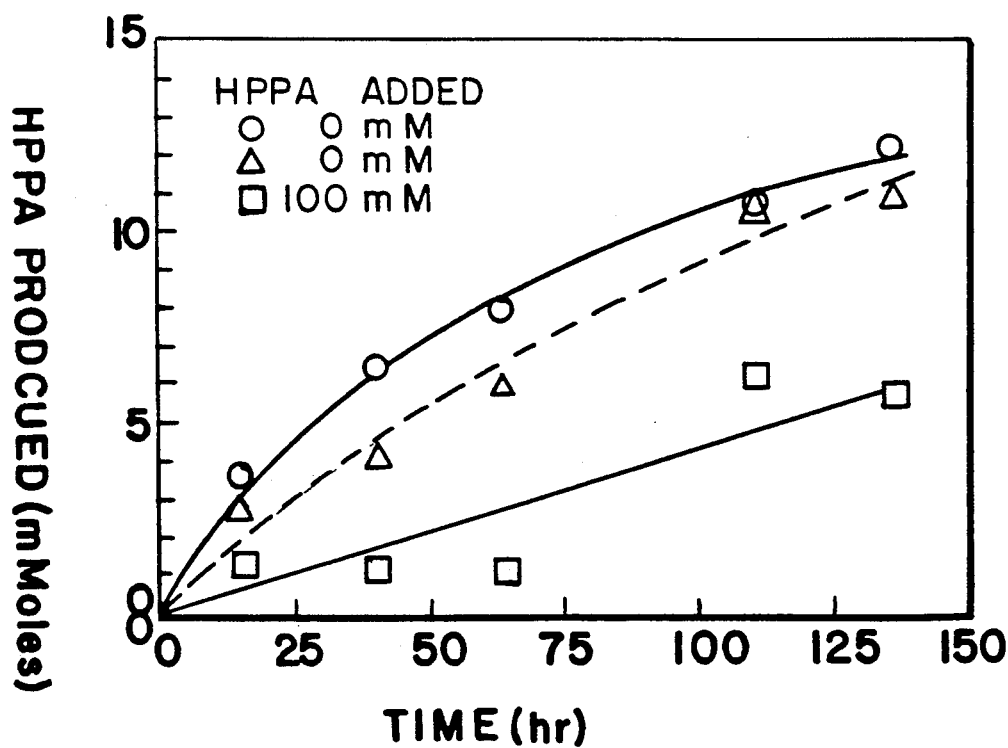

The products of the hydrolysis of HPPA-Me, methanol and HPPA, were tested independently to determine their effects on the activity of the enzyme. The introduction of 0.5 equivalents of methanol at the start of the hydrolysis reaction resulted in a 39% decrease in activity of the enzyme against HPPA-Me. Addition of various amounts (R)-HPPA at the beginning of a hydrolysis reaction resulted in a 10-67% reduction in enzyme activity (FIG. 16). Increasing concentrations of HPPA showed a corresponding decrease in the activity of the enzyme.

Figure 17:
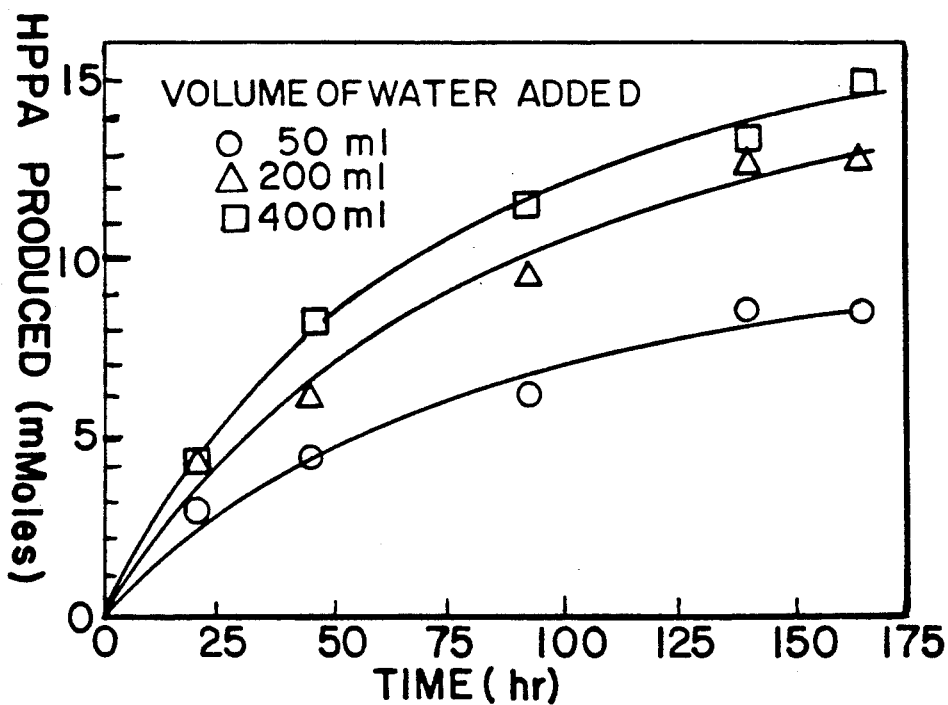

The effect of dilution on the activity of the enzyme in a two phase system is given in FIG. 17. The rate is increased substantially by the dilution of the aqueous phase, although the ester resides nearly exclusively in the toluene layer.

Figure 18:
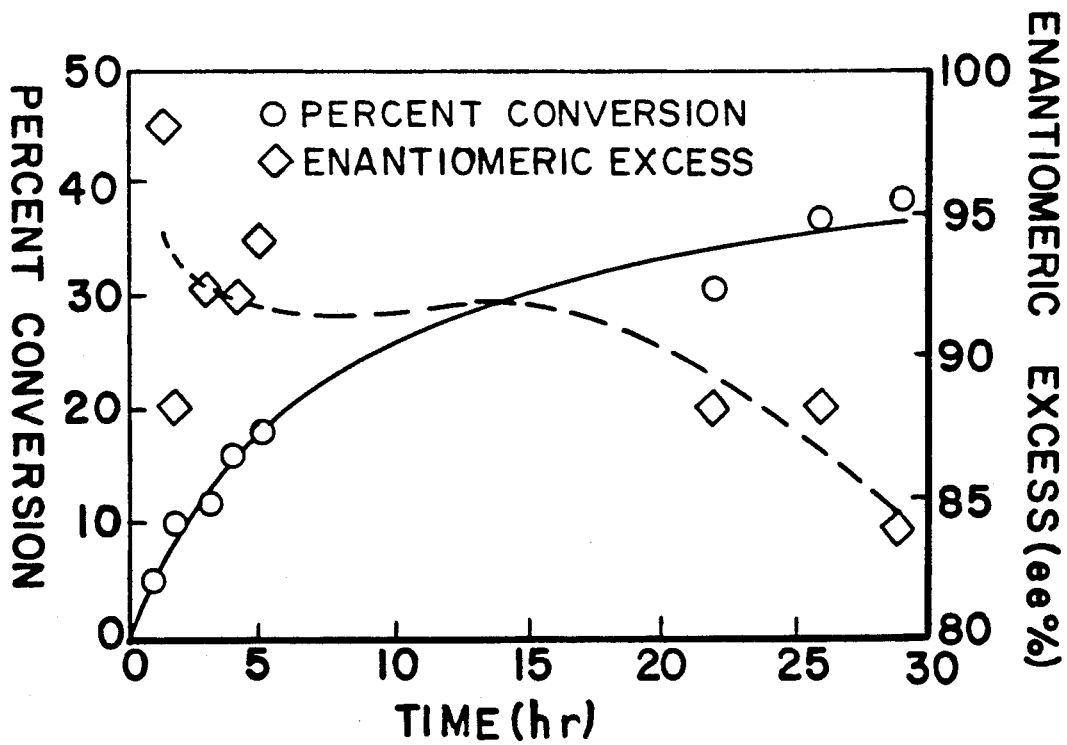

In a kilogram scale reaction, applying the optimum conditions obtained above, the optical purity of the (R)-HPPA produced was 84% ee at 39% conversion, FIG. 18. The optical purity of the product obtained in this manner could be increased by recrystallization from a number of organic solvents including ethyl acetate and chloroform.

TABLE 37

Activity and Enantiospecificity of Lipase MY as a Function of the pH of Solution[a]

| pH | % conversion | Activity (umol/hr/mg) | % ee |
|---|---|---|---|
| 3.0 | 34 | 96 | 89 |
| 4.0 | 33 | 95 | 88 |
| 4.5 | 35 | 100 | 87 |
| 5.0 | 36 | 103 | 86 |
| 5.5 | 38 | 109 | 84 |
| 6.0 | 42 | 121 | 80 |
| 6.5 | 47 | 134 | 78 |
| 7.0 | 46 | 133 | 77 |
| 7.5 | 50 | 142 | 76 |
| 8.0 | 51 | 147 | 67 |
| 8.5 | 48 | 136 | 52 |

[a](R,S)-HPPA-Me, 196 mg. 100 ml of phosphate buffer at the indicated pH and 0.5 ml of a 1 mg/ml solution of lipase MY prepared by centrifuging at 7500 RPM for 20 minutes were allowed to react for 7 hr and analyzed by HPLC.

TABLE 38

Effect of Saturation with (R,S)-HPPA-Me on Enzyme Activity.[a]

| Time (Hrs) | [HPPA] (mM) | Activity uM/hr/mg (% conversion) | (R)-HPPA ee (%) |
|---|---|---|---|
| 18 | 19.8 | 1.1 (2) | 18 |
| 45 | 41.4 | .92 (4) | 8 |
| 65 | 66.2 | 1.0 (7) | 4 |
| 114 | 114 | .8 (11.4) | 6 |

[a](R,S)-HPPA-Me (1.5 moles) in 1 L of 0.5M phosphate buffer, pH 7.0 at 40-45° C. and 1 g of Lipase MY were stirred for 114 hours and samples were analyzed by HPLC as noted in FIG. 1.

TABLE 39

Effect of Temperature on Activity and Stereoselectivity.[a]

| Time (Hrs) | 12° C. [HPPA] | 12° C. ee (%) | 21° C. [HPPA] | 21° C. ee (%) | 35° C. [HPPA] | 35° C. ee (%) | 45° C. [HPPA] | 45° C. ee (%) |
|---|---|---|---|---|---|---|---|---|
| 1 | — | — | — | — | 28 | 94 | 31 | 92 |
| 3 | — | — | — | — | 67 | 96 | 52 | 92 |
| 20 | — | — | — | — | 154 | 92 | 101 | 90 |
| 31 | 115 | 90 | 178 | — | — | — | — | — |
| 44 | 201 | 92 | 255 | 94 | 209 | 92 | 162 | 90 |
| 51 | 202 | 92 | 269 | 94 | — | — | — | — |
| 69 | 227 | 92 | 248 | 90 | — | — | — | — |

TABLE 39-continued

| | Effect of Temperature on Activity and Stereoselectivity.[a] | | | | | | | |
|---|---|---|---|---|---|---|---|---|
| Time | 12° C. | | 21° C. | | 35° C. | | 45° C. | |
| (Hrs) | [HPPA] | ee (%) | [HPPA] | ee (%) | [HPPA] | ee (%) | [HPPA] | ee (%) |
| 88 | 253 | 92 | 289 | 88 | — | — | — | — |

[a]HPPA-Me, 294 g, 1 L of 1M ammonium acetate, pH 7.05, 150 ml of toluene and 2 g of lipase MY were maintained at the indicated temperature. Samples of the aqueous layer were analyzed as in FIG. 1.

The accompanying drawings are as follows:

List of Figures

FIG. 1 SDS-PAGE of Lipase MY, Lipase AY and Biocatalyst lipase.

FIG. 2 IEF gel, pI 3-9 of commercial C. rugosa lipases.

FIG. 3 SP-TrisAcryl M chromatography of Lipase MY.

FIG. 4 IEF gel, pI 3-9 of SP-TrisAcryl M Lipase MY column fractions.

FIG. 5 SP-Sephadex chromatography of Lipase MY.

FIG. 6 IEF GEL, pI 3-9 of SP-TrisAcryl LS Lipase MY column fractions.

FIG. 7 SP-TrisAcryl LS chromatography of Lipase MY.

FIG. 8 Effect of organic acids on the immobilization of Lipase MY.

FIG. 9 Effect of stearic acid (0-20%) on lipase MY immobilization.

FIG. 10 Effect of stearic acid (0-10%) on lipase MY immobilization.

FIG. 11 Stability of Immobilized lipase CSC-1.

FIG. 12 SDS-PAGE of C. rugosa lipases, CSC-2 and ENZECO Rxx.

FIG. 13 Preparative isoelectric focusing of Lipase MY

FIG. 14 Chromatogram

FIG. 15 Conversion versus Enantiomeric Excess

FIG. 16 HPPA Produced versus Time

FIG. 17 HPPA Produced versus Time

FIG. 18 Percent Conversion versus Time

FIGURE LEGENDS

FIG. 1 SDS-PAGE of Lipase MY, Lipase AY, and Biocatalyst lipase. Lanes 1 and 4, Biocatalyst lipase; lanes 2 and 5, lipase AY (Amano); lanes 3 and 6, lipase MY (Meito Sangyo). (see Ex.1)

FIG. 2 IEF gel, pI 3-9 of commercial C. rugosa lipases. Gel was run for 390 volt-hr. Lane 1, Sigma lipase; lane 2, lipase OF; lane 3, Lipase MY; lane 4, Lipase AY; lane 5, Biocatalyst lipase; lane 6, pI standards. (see Ex.10)

FIG. 3 SP-TrisAcryl M chromatography of Lipase MY. (C. rugosa). Lipase MY (1.0gm) in 25 mM NaH$_2$PO$_4$ pH 3.3 was applied to a 2.5 ×20 cm column equilibrated with 25 mM NaH$_2$PO$_4$ pH 3.3. Protein was eluted as two fractions using citrate phosphate buffer pH 4.75 followed by citrate phosphate buffer pH 6.80. (see Ex. 11).

FIG. 4 IEF gel, pI 3-9 of SP-TrisAcryl M lipase MY column fractions. Lane 1, Lipase MY; Lane 2, pass through fraction; lane 3, peak 1 protein; lane 4, peak 2 protein; lane 5, peak 3 protein; lane 6, pI standards 3-9. Gel was silver stained. (see Ex.11).

FIG. 5 SP-Sephadex chromatography of Lipase MY (C. rugosa). Lipase MY (1.30gm) in citrate-phosphate buffer pH 3.3 was applied to a 2.5×20 cm column in the same buffer. Stepwise elution was carried out with citrate-phosphate buffer pH 4.70, followed by citrate-phosphate buffer pH 6.80.

FIG. 6 IEF GEL, pI 3-9 of SP-TrisAcryl LS lipase MY column fractions. Lanes 1 and 8 are IEF pI standards; lanes 2 and 3 are samples of Lipase MY; lanes 4 and 5 are protein pool eluted with pH 6.80 buffer (CSC-1); lanes 6 and 7 are the protein pool eluted with pH 4.75 (CSC-2). Gel was silver stained. (see Ex.13).

FIG. 7 SP-TrisAcryl LS chromatography of Lipase MY. The column (9 X 45 cm) was equilibrated in 25 mM sodium phosphate, pH 3.2. Lipase MY (150 gm) was dissolved in 3.0 liter of 25 m NaH$_2$PO$_4$ pH 6.5, the solids were removed and the pH adjusted to 3.0. Details of elution are described in the legend to FIG. 3. (see Ex.14).

FIG. 8 Effect of organic acids on the immobilization of Lipase MY. Lipase MY (0.45 gm), Amberlite DP-1 (0.9g) and XAMA-7 (100 mg) were mixed in 10 ml of toluene containing 30-50 mg of a saturated acid. After curing, hydration and washing, the enzyme was assayed for HPPA-Me ester hydrolytic activity. (see Ex.26).

FIG. 9 Effect of stearic acid (0-20%) on lipase MY immobilization. Lipase MY was immobilized as described in legend to FIG. 8 using various stearic acid concentrations. HPPA-Me ester hydrolytic activity was assayed. (see Ex.27).

FIG. 10 Effect of stearic acid (0-10%) on lipase MY immobilization. Lipase MY and DP-1 resin were mixed and lyophilized from a pH 4.5 buffer prior to addition to the toluene, containing the XAMA-7 and the stearic acid. Solvent was evaporated to effect polymerization. Activity was assayed as in legend to FIG. 8. (see Ex.28).

FIG. 11 Stability of Immobilized Lipase CSC-1. Isolated lipase CSC-1, immobilized using XAMA-7 and Amberlite DP-1 resin (see Ex.13) was used as a catalyst to convert 25 mM HPPA-Me ester. The column (1×24 cm) was operated at 0.75 ml/min in the presence of 1.0 gm/l sodium dithionite. Enzymatic activity was assayed daily. (see Ex.33).

FIG. 12 SDS-PAGE of C. rugosa lipases, CSC-2 and ENZECO Rxx. Protein samples were separated on a 8-15% polyacrylamide gradient gel. Lane 1, Enzeco Rxx lipase; lane 2, CSC-2 lipase; lane 3, molecular weight standards. The major 60K dalton lipase band is marked by an arrow (see Ex. 57).

FIG. 13 Preparative isoelectric focusing of lipase MY. Lipase MY (400 mg) was desalted and solids removed. Sample was combined with 2 ml of ampholytes (pH 2.5-5) and focused at 12 watts at 4° C. for 4 hours.

FIG. 14 Chromatogram of (R,S)-HPPA, (R)-HPPA and (S)-HPPA. Chromatographic conditions: Column, Resolvosil BSA-7, Macherey-Nagel, mobile phase 5% n-propanol (v/v) in 10 mM KH$_2$PO$_4$, pH 5.0 buffer; flow rate, 2.7 ml min$^{-1}$, temperature 22° C., UV detection at 220 nm.

FIG. 15 Effect of approaching theoretical limit of conversion on ee.

FIG. 16 Effect of HPPA on the hydrolysis of HPPA-Me. Ammonium acetate, 200 ml, 0.04 M, pH 7.0, was combined with 30 ml of toluene, 40 mmoles HPPA-Me, 25 mg of Lipase MY, and the indicated quantity of (R,S)-HPPA. The reactions were sampled as indicated and analyzed as in FIG. 1.

FIG. 17 Effect of dilution on enzyme rate. The indicated amount of water, 0.04 moles HPPA-Me, 0.04 moles ammonium acetate, pH 7, 30 ml of toluene and 25 mg Lipase MY in 25 ml of water were allowed to react for 164 hours. Samples of the aqueous layer were analyzed as in FIG. 1.

FIG. 18 Kilogram scale production of (R)-HPPA. Lipase MY, 25 g, 1 L of 0.2 N ammonium acetate, pH 6.5, 9 L of water, 2.5 L of toluene and 1.176 kg of (R,S)-HPPA-Me were allowed to react for 29 hrs. Samples were analyzed by HPLC as in FIG. 1.

As will be evident from the foregoing, various modifications are contemplated in the practice of the invention. Accordingly, the scope of the invention is defined in the following claims wherein:

We claim:

1. A process for stereoselectively hydrolyzing racemic mixtures of esters of 2-substituted acids, other than 2-halo propionic acids, transesterifying esters or acids or esterifying acids or alcohols, at high enantiomeric excess, comprising the steps of contacting said racemic mixture, ester, acid or alcohol with an immobilized isozyme of Lipase MY or AY of *Candida rugosa* in an organic solvent.

2. The process of claim 1 wherein the isozyme of Lipase My or AY of *Candida rugosa* has an N terminal amino acid sequence of: Ala-Pro-Thr-Ala-Lys-Leu-Ala-Asn-Gly-V-Thr-Ile-Thr-Gly -Leu-Asn-Ala-Ile-Ile-Asn-Glu-Ala-Phe-Leu-Gly-Ile-Pro-Phe-Ala-Glu -Pro-Pro-Val-Gly-Asn-P wherein V is an amino acid and P is the remaining portion of the amino acid sequence of the isozyme.

3. The process of claim 1 wherein the isozyme of Lipase MY or AY of *Candida rugosa* has an N terminal amino acid sequence of: Ala-Pro-Thr-Ala-Thr-Leu-Ala-Asn-Gly-Asp-Thr-Ile-Thr -Gly-Leu-Asn-Ala-Ile-Ile-Asn-Glu-Ala-Phe-Leu-Gly-Ile-W-X-Ala-Glu -Pro-Pro-Y-Z-Asn-Leu-Phe-Ile-ZZ-Leu-P wherein W, X, Y, Z and ZZ are amino acids and P is the remaining portion of the amino acid sequence of the isozyme.

4. The process of claim 1 wherein the ester is an ester of 2-aryloxypropionic acid.

5. The process of claim 1 wherein the ester is an ester of 2-(4-hydroxyphenoxy) propionic acid.

6. The process of claim 1 wherein the ester is the methyl or ethyl ester of 2-(4-hydroxyphenoxy) propionic acid.

7. The process of claim 1 wherein the ester is an ester of 2-arylpropionic acid.

8. The process of claim 1 wherein the ester is an ester of ketoprofen.

9. The process of claim 8 wherein the ketoprofen ester is an alkyl ester.

10. The process of claim 8 wherein the ketoprofen ester is a methyl, ethyl, n-propyl, n-butyl or n-octyl ester.

11. The process of claim 8 wherein the ketoprofen ester is a halogen-substituted ester.

12. The process of claim 8 wherein the ketoprofen ester is a 2-chloroethyl, 2,2,2-trichloroethyl or 2,2,2-trifluoroethyl ester.

13. The process of claim 8 wherein the ketoprofen ester is a hydroxylated ester.

14. The process of claim 8 wherein the ketoprofen ester is a monoglyceryl, b 2-hydroxyethyl, diethylene glycol or triethylene glycol monomethyl ester.

15. The process of claim 1 wherein the ester is an ester of ibuprofen.

16. The process of claim 1 wherein the ester is an ester of fenoprofen.

17. The process of claim 1 wherein the ester is an ester of 2-phenylpropionic acid.

18. The process of claim 1 wherein the ester is an ester of indoprofen.

19. The process of claim 1 wherein the immobilized isozyme is used with an additive of fatty acids or fatty acid esters.

20. The process of claim 19 wherein the additive is selected from the group consisting of oleate esters, vegetable oils, animal oils and oleate containing surfactants.

21. The process of claim 19 wherein the additive is oleic acid.

22. The process of claim 19 wherein the additive is linoleic acid methyl ester.

23. The process of claim 1 wherein the isozyme is immobilized in the presence of stearic acid.

* * * * *